(12) United States Patent
Jin et al.

(10) Patent No.: US 10,683,553 B2
(45) Date of Patent: Jun. 16, 2020

(54) METHOD FOR DETERMINING SENSITIVITY TO SIMULTANEOUS INHIBITOR AGAINST PARP AND TANKYRASE

(71) Applicant: THE ASAN FOUNDATION, Seoul (KR)

(72) Inventors: Dong Hoon Jin, Seoul (KR); Seung Woo Hong, Seoul (KR); Jai Hee Moon, Seoul (KR); Jae Sik Shin, Seoul (KR); Seung Mi Kim, Seoul (KR); Dae Hee Lee, Seoul (KR); Eun Young Lee, Seoul (KR); Jung Shin Lee, Seoul (KR); Bong Choel Kim, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 39 days.

(21) Appl. No.: 15/742,408

(22) PCT Filed: Jul. 6, 2016

(86) PCT No.: PCT/KR2016/007333
§ 371 (c)(1),
(2) Date: Jan. 5, 2018

(87) PCT Pub. No.: WO2017/007241
PCT Pub. Date: Jan. 12, 2017

(65) Prior Publication Data
US 2018/0327851 A1    Nov. 15, 2018

(30) Foreign Application Priority Data
Jul. 6, 2015    (KR) .......................... 10-2015-0095924

(51) Int. Cl.
*C12Q 1/68* (2018.01)
*C12Q 1/6886* (2018.01)

(52) U.S. Cl.
CPC ............. *C12Q 1/6886* (2013.01); *C12Q 1/68* (2013.01); *C12Q 2600/106* (2013.01)

(58) Field of Classification Search
None
See application file for complete search history.

(56) References Cited

U.S. PATENT DOCUMENTS 8,815,891 B2    8/2014   Kim et al.
10,464,919 B2   11/2019  Lee et al.

FOREIGN PATENT DOCUMENTS

EP    2036990 B1       4/2014
WO    2013164061 A1    11/2013

OTHER PUBLICATIONS

Syvanen. Dec. 2001. vol. 2. p. 930-942 (Year: 2001).*
Thorsell et al. J. Med. Chem. 2017, 60, 1262-1271 (Year: 2017).*
Mariotti et al. British Journal of Pharmacology (2017) 174 4611-4636 4611 (Year: 2017).*
Osherovich et al. SciBX 6(15); doi:10.1038/scibx.2013.353 Published online Apr. 18, 2013; 2 pages. (Year: 2013).*
Kweekel et al. (British Journal of Cancer (2009) 101, 357-362) (Year: 2009).*
The Cancer Genome Atlas Network (Nature. Jul. 18, 2012;487(7407):330-7 (Year: 2012).*
West et al. (Clinical Oncology (2007) 19: 470e480) (Year: 2007).*
Begg et al. (Nature Reviews, vol. 11, pp. 239-253) (Year: 2011).*
Yoon et al. (Cancer Chemother Pharmacol (2011) 68:863-870) (Year: 2011).*
Kuhmann et al. (Human Molecular Genetics, 2014, vol. 23, No. 8 2043-2054) (Year: 2014).*
Kubota, et al., "Low ATM protein expression and depletion of p53 correlates with olaparib sensitivity in gastric cancer cell lines", Cell Cycle 13:13, Jul. 1, 2014, pp. 2129-2137.
Seimiya, "The telomeric PARP, tankyrases, as targets for cancer therapy", British Journal of Cancer, 94, 2006, pp. 341-345.
Williamson, et al., "Enhanced cytotoxicity of PARP inhibition in mantle cell lymphoma harbouring mutations in both ATM and p53", EMBO Molecular Medicine 4, 2012, pp. 515-527.

* cited by examiner

*Primary Examiner* — Juliet C Switzer
(74) *Attorney, Agent, or Firm* — Stoel Rives LLP

(57) ABSTRACT

The present invention relates to a method for determining sensitivity to a simultaneous inhibitor against poly ADP ribose polymerase (PARP) and Tankyrase. According to the present invention, a colorectal treatment effect can be maximized by sorting patients having sensitivity to the simultaneous inhibitor against PARP and Tankyrase.

4 Claims, 20 Drawing Sheets

Specification includes a Sequence Listing.

METHOD FOR DETERMINING SENSITIVITY TO SIMULTANEOUS INHIBITOR AGAINST PARP AND TANKYRASE

RELATED APPLICATIONS

This application is a United States National Phase entry of International Application No. PCT/KR2016/007333 filed Jul. 6, 2016, which claims the benefit of Korean Patent Application No. 10-2015-0095924 filed Jul. 6, 2015. The entire contents of both of the foregoing applications are hereby incorporated by reference herein.

TECHNICAL FIELD

The present disclosure was made under the Task No. HI06C0868 under the support of the Ministry of Health and Welfare of the Republic of Korea. The research management specialized institute of the above task is the Korea Health Industry Development Institute, the research project name is "Leading Specialization Research Project," the research task name is "Development of anticancer drugs targeting Wnt signaling mechanism," and the research institute is the Institute for Innovative Cancer Research of Asan Medical Center in Seoul. The research period is from Dec. 1, 2013 to Nov. 30, 2016.

The present invention relates to a method for determining susceptibility to a simultaneous inhibitor against PARP (Poly ADP Ribose Polymerase) and Tankyrase.

BACKGROUND

Biomarkers are defined as 'indicators that can objectively measure and evaluate the response of drugs to normal biological processes, disease progression, and treatment methods'. Recently, with the development of gene analysis technology, research on the relationship between a specific gene mutation and a specific disease has increased, so that a biomarker can be re-defined as a molecular and biological indicator that covers the differences in gene and genetic mutation, the differences in expressions of RNA, protein, and metabolites.

In addition, the Companion Diagnostic Device (CDx), by which the susceptibility of biomarkers can be determined, has been developed to classify patients so that the treatment effect of medicines can be maximized or side effects of medicines for more effective treatment can be minimized.

The large intestine is a long tube-like digestive tract of about 150 cm connected from the end of the small intestine to the anus. It is divided into cecum, colon, rectum and anal canal. Malignant tumors arising in the colon and rectum are colon cancer. The majority of colon cancers are adenocarcinoma (i.e., adenocarcinoma), which is a cancer of the glandular cells in the mucous membranes. In addition, the protopathy such as lymphomas, malignant carcinoid tumors, leiomyosarcoma, etc. may occur.

Numerous theses and patent documents are referenced and cited throughout this specification. The disclosures of the cited theses and patent documents are incorporated herein by reference in their entirety to better illustrate the state of the art to which the present disclosure pertains and the content of the present invention.

Technical Problem

The present inventors have attempted to develop a method for determining susceptibility to a simultaneous inhibitor against PARP and Tankyrase to maximize the treatment effect of the simultaneous inhibitor against PARP (Poly ADP Ribose Polymerase) and Tankyrase, which are colon cancer drugs. As a result, the present inventors have completed the present invention by confirming that the treatment effect of a simultaneous inhibitor against the PARP and the Tankyrase can be maximized when a p53 genotype of the colorectal cancer cells isolated from a patient with colorectal cancer is a normal type and a genotype of LIG4 is a mutant type.

Accordingly, it is an object of the present invention to provide a method for determining susceptibility to a simultaneous inhibitor against PARP and Tankyrase.

Another object of the present invention is to provide a kit for determining susceptibility to a simultaneous inhibitor against PARP and Tankyrase.

Other objects and advantages of the present invention will become more apparent from the following detailed description of the invention, claims and drawings.

Technical Solution

According to one aspect of the present invention, there is provided a method for determining susceptibility to a simultaneous inhibitor against PARP (Poly ADP Ribose Polymerase) and Tankyrase, the method comprises the following steps of:

(a) isolating colorectal cancer cells from patient with colorectal cancers;

(b) isolating nucleic acid molecules of colorectal cancer cells of the step (a); and (c) identifying genotypes of a p53 gene and an LIG4 (DNA ligase 4) gene in the nucleic acid molecule of the step (b), wherein where the genotype of the p53 gene is a normal type and the genotype of the LIG4 gene is a mutant type, it is determined that the patient is susceptibility to a simultaneous inhibitor against PARP and Tankyrase.

The present inventors have attempted to develop a method for determining susceptibility to a simultaneous inhibitor against PARP and Tankyrase to maximize the treatment effect of the simultaneous inhibitor against PARP (Poly ADP Ribose Polymerase) and Tankyrase, which are colon cancer drugs. As a result, the present inventors have confirmed that the treatment effect of the simultaneous inhibitors against PARP and the Tankyrase can be maximized when the p53 genotype of the colorectal cancer cells isolated from a patient with colorectal cancer is a normal type and the genotype of LIG4 is a mutant type.

The method for determining susceptibility to a simultaneous inhibitor against PARP and Tankyrase according to the present invention will be described in detail step by step.

Step (a) Isolation of Colorectal Cancer Cells

First, in order to obtain colorectal cancer cells from a patient with a colorectal cancer, they could be obtained by cutting colorectal cancer tissue and then treating it with an appropriate proteolytic enzyme.

The proteolytic enzyme may be one or more enzymes selected from the group consisting of papain, pancreatin, trypsin, chymotrypsin, pepsin, streptokinase, streptodornase, ficain, carboxypeptidase, aminopeptidase, chymopapain, bromelin, and subtilisin.

Step (b) Isolation of Nucleic Acid Molecules

Next, nucleic acid molecules of colon cancer cells of the step (a) are isolated.

As used herein, the term "nucleic acid molecule" has a comprehensive meaning inclusive of DNA (gDNA and cDNA) and RNA molecules, and the nucleotide, which is a basic constituent unit in the nucleic acid molecule, includes not only natural nucleotides, but also analogues in which sugar or base moieties are modified (Scheit, Nucleotide Analogs, John Wiley, New York (1980); Uhlman and Peyman, Chemical Reviews, 90: 543-584 (1990)).

In the method of the present invention, the nucleic acid molecule can be obtained from colon cancer cells isolated from colon cancer tissue of a colon cancer patient.

Step (c) Identification of p53 and LIG4 Genotypes

Next, as the step of confirming the genotypes of the p53 gene and LIG4 (DNA ligase 4) gene of the nucleic acid molecule of the step (b), in which when the genotype of the p53 gene is a normal type and the genotype of the LIG4 gene is a mutant type, there is susceptibility to PARP and Tankyrase inhibitors.

In order to confirm the genotypes, when the starting material is gDNA, the isolation of gDNA may be carried out according to conventional methods known in the art (see Rogers & Bendich (1994)). When the starting material is mRNA, the total RNA is isolated by a conventional method known in the art (see Sambrook, J. et al., Molecular Cloning. A Laboratory Manual, 3rd ed. Cold Spring Harbor Press (2001); Ausubel, F. M. et al., Current Protocols in Molecular Biology, John Willey & Sons (1987); and Chomczynski, P. et al., Anal. Biochem. 162:156(1987)). The isolated total RNA is synthesized into cDNA using reverse transcriptase. Since the total RNA is isolated from animal cells, it has a poly-A tail at the end of mRNA. cDNA can be easily synthesized using oligo dT primers and reverse transcriptase using such a sequence characteristic (see PNAS USA, 85: 8998 (1988); Libert F, et al., Science, 244: 569 (1989); and Sambrook, J. et al., Molecular Cloning. A Laboratory Manual, 3rd ed. Cold Spring Harbor Press (2001)).

In the method of the present invention, the step (c) may be carried out by applying various methods known in the art used for genotyping of genotype.

According to an embodiment of the present invention, the step (c) may be performed by DNA sequencing, Polymerase Chain Reaction (PCR), Restriction Fragment Length Polymorphism (RFLP), Random Amplified Polymorphic Detection (RAPD), Amplified Fragment Length Polymorphism Detection (AFLPD), ASO (Allele Specific Oligonucleotide) probe or DNA microarray.

If the genotype of the p53 gene is a normal type and the genotype of the LIG4 gene is a mutant type, it is determined to have susceptibility to PARP and Tankyrase inhibitors.

According to an embodiment of the present invention, the p53 gene includes a nucleotide sequence, the sequence listing represented by SEQ ID NO: 1 when the genotype thereof is a normal type, and the LIG4 gene includes a nucleotide sequence, the sequence listing represented by SEQ ID NO: 2 when the genotype thereof is a normal type.

When the genotype of the LIG4 gene is a mutant type, it includes the mutation of the nucleotide sequence of LIG4.

According to another embodiment of the present invention, where the LIG4 gene is one or more sequence variants selected from the group consisting of a substitution of cytosine to thymine at position 8, a substitution of cytosine to thymine at position 26, a substitution of guanine to adenine at position 833 and a substitution of thymine to cytosine at position 1704 of SEQ ID NO: 2, it is determined that the genotype is a mutant type.

When the genotype of the LIG4 gene is a mutant type, it includes the mutation of the amino acid sequence of LIG4.

According to one embodiment of the present invention, where the LIG4 gene is one or more sequence variants selected from the group consisting of a substitution of alanine to valine at position 3, a substitution of threonine to isoleucine at position 9, a substitution of arginine to histidine at position 278 and a substitution of thymine of aspartic acid (GAT) to cytosine at position 568 of SEQ ID NO: 3, it is determined that the genotype is a mutant type.

When the thymine base of aspartic acid (GAT), which is the 568th amino acid, is substituted with cytosine, the thymine base in the GAT, which is a codon that encodes for aspartic acid, the 568th amino acid, is an aspartic acid (GAC) substituted with cytosine.

As the step of confirming the genotypes of the p53 gene and LIG4 (DNA ligase 4) gene of the nucleic acid molecule, when the genotype of the p53 gene is a normal type and the genotype of the LIG4 gene is a mutant type, it is determined to have susceptibility to PARP and Tankyrase inhibitors.

According to one embodiment of the present invention, the IUPAC name of the PARP and Tankyrase inhibitor, Compound A, is 8-[(dimethylamino)methyl]-10-ethoxy-1,2,3,4-tetrahydrobenzo[h][1,6]naphthyridin-5(6H)-one, and the IUPAC name of Compound B is 6-{4-[(5-oxo-1,2,3,4,5,6-hexahydrobenzo[h][1,6]naphthyridin-8-yl)methyl]piperazin-1-yl}nicotinonitrile.

In accordance with another aspect of the present invention, the present disclosure provides a kit for determining susceptibility to a simultaneous inhibitor against PARP (Poly ADP Ribose Polymerase) and Tankyrase, in which the kit includes: (a) a primer or a probe that specifically binds to a nucleotide sequence encoding a p53 gene; and (b) a primer or a probe that specifically binds to a nucleotide sequence encoding an LIG4 (DNA ligase 4) gene.

As used herein, the term "primer" refers to a single strand oligonucleotide that can act as a starting point for template-directed DNA synthesis under suitable conditions (i.e., four other nucleoside triphosphates and polymerization enzymes) in a suitable buffer at a suitable temperature. The suitable length of the primer is typically 15 to 30 nucleotides, although it varies with various factors such as temperature and use of the primer. Short primer molecules generally require lower temperatures to form a sufficiently stable hybrid complex with the template.

The sequence of the primer does not need to have a sequence completely complementary to a partial sequence of the template, and it is sufficient that the primer has sufficient complementarity within a range capable of hybridizing with the template and acting as a unique primer. Therefore, the primer in the present disclosure does not need to have a perfectly complementary sequence to the above-mentioned nucleotide sequence which is a template, and it is sufficient that the primer has sufficient complementarity within a range capable of hybridizing with the gene sequence and acting as a primer. The design of such a primer can be easily carried out by those skilled in the art with reference to the nucleotide sequence described above, for example, by using a program for primer design (e.g., PRIMER 3 program).

As used herein, the term "probe" refers to a linear oligomer of natural or modified monomers or linkages, including deoxyribonucleotides and ribonucleotides and can specifically hybridize to a target nucleotide sequence, and are naturally present or artificially synthesized. The probe of the present disclosure is preferably a single strand and is an oligodioxyribonucleotide.

The nucleotide sequence of the marker of the present disclosure to be referred to in the preparation of the primer or probe can be confirmed by GenBank. For example, the p53 of the present disclosure has the nucleotide sequence having GenBank Accession No. NM_000546.5 and the LIG4 has the nucleotide sequence having GenBank Accession No. NM_002312.3, and primers or probes can be designed with reference to this sequence.

According to an embodiment of the present invention, the nucleotide sequence encoding the p53 gene is represented by SEQ ID NO: 1 and the nucleotide sequence encoding the LIG4 gene is represented by SEQ ID NO: 2.

According to another embodiment of the present invention, in order to detect the mutant LIG4 gene, a primer pair represented by SEQ ID NOS.: 8 and 9, a pair of primers represented by SEQ ID NOS.: 10 and 11 and a pair of primers represented by SEQ ID NOS.: 12 and 13 are used.

Advantageous Effects

The features and advantages of the present invention are summarized as follows:

(a) The present invention provides a method and a kit for determining susceptibility to a simultaneous inhibitor against PARP (poly ADP Ribose Polymerase) and Tankyrase.

(b) The present invention can maximize the treatment effect of colon cancer by classifying patient groups with susceptibility to a simultaneous inhibitor against PARP and Tankyrase.

SUMMARY

Additional aspects and advantages will be apparent from the following detailed description of preferred embodiments, which proceeds with reference to the accompanying drawings.

DETAILED DESCRIPTION OF PREFERRED EMBODIMENTS

Figure 1:
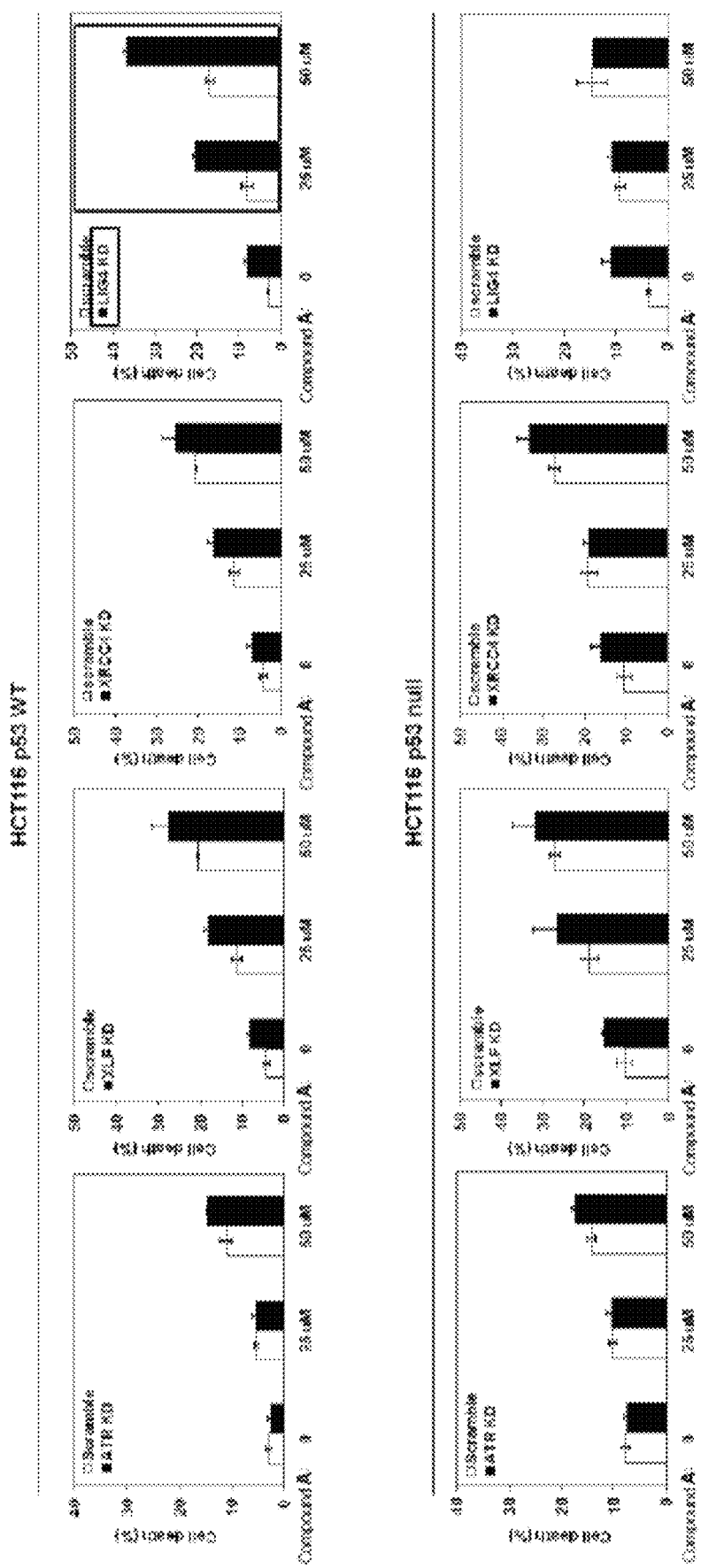
FIG. 1 illustrates the results of analysis of the anti-cancer susceptibility of Compound A, and the relevance of the presence or absence of p53 and the DNA repair-related genes (ATR, XLF, XRCC4, and LIG4) of Compound A, in which Compound A is a simultaneous inhibitor against PARP/Tankyrase in the human colon cancer cell line HCT116.

It will be obvious to those having skill in the art that many changes may be made to the details of the above-described embodiments without departing from the underlying principles of the invention. The scope of the present invention should, therefore, be determined only by the following claims.

Modes of the Invention

Hereinafter, the present disclosure will be described in more detail with reference to the examples. It is to be understood by those skilled in the art that these embodiments are only for describing the present disclosure in more detail and that the scope of the present disclosure is not limited by these embodiments in accordance with the gist of the present invention.

The IUPAC name of the novel PARP/Tankyrase simultaneous inhibitor Compound A used in the present disclosure is 8-[(dimethylamino)methyl]-10-ethoxy-1,2,3,4-tetrahydrobenzo[h][1,6]naphthyridin-5(6H)-one, and the IUPAC name of Compound B is 6-{4-[(5-oxo-1,2,3,4,5,6-hexahydrobenzo[h][1,6]naphthyridin-8-yl)methyl]piperazin-1-yl}nicotinonitrile.

Example 1: IC50 Analysis of Compound A as a PARP/Tankyrase Simultaneous Inhibitor The present inventors conducted an in vitro cell base assay to analyze the anticancer activity of Compound A, which is a novel PARP/Tankyrase simultaneous inhibitor, in 18 human colon cancer cell lines (Korean Cell Line Bank and ATCC purchased), and the cell viability and $IC_{50}$ of the cell lines for Compound A, the novel PARP/Tankyrase simultaneous inhibitor, were measured.

As the experimental conditions and methods, a total of 18 human colon cancer cell lines were cultured in RPMI1640 (Roswell Park Memorial Institute 1640; 10% FBS, 1% penicillin/streptomycin), and each cell line was cultured in 96 well plate for $2\times10^3$ per well at 37° C. for 24 hours and the novel PARP/Tankyrase simultaneous inhibitor, Compound A, was diluted by a multiple of 2 at a maximum of 100 μM and a minimum of 0.390625 μM (100 μM, 50 μM, 25 μM, 12.5 μM, 6.25 μM, 3.125 μM, 1.5625 μM, 0.78125 μM and 0.390625 μM). After the treatment, it was cultured at 37° C. for 72 hours. As for the drug treatment group and non-treatment group, the cell viability of each cell line was measured by MTS analysis (Promega, CellTiter 96 AQeous One Solution) and the IC50 of each cell line was measured using the PRISM program.

Experiment Result

As a result of analyzing $IC_{50}$ using MTS analysis of each of the 18 human colon cancer cell lines treated with Compound A, a novel PARP/Tankyrase simultaneous inhibitor, the significant $IC_{50}$ values of Compound A were shown in the cell lines of 10 species (HCT116, HT29, RKO, LoVo, LS174T, Colo201, Colo205, Colo320HSR, HCT8 and Caco-2).

TABLE 1

| Colon cancer cell line | Compound A $IC_{50}$ (uM) | Colon cancer cell line | Compound A $IC_{50}$ (uM) |
|---|---|---|---|
| Colo320 | 8.27 | HCT8 | 39.50 |
| Ls174T | 12.19 | DLD-1 | 85.57 |
| HCT116 | 13.18 | SW620 | 96.65 |
| LoVo | 18.57 | SW480 | >100 |
| Caco-2 | 19.24 | SW1417 | >100 |
| RKO | 23.71 | KM12C | >100 |
| Colo205 | 24.45 | SW48 | >100 |
| Colo201 | 28.43 | HCT-15 | >100 |
| HT-29 | 32.21 | Ls1034 | >100 |

Example 2: Anticancer Susceptibility of Compound A According to p53 Genotype The present inventors analyzed the correlation of 18 human colon cancer cell lines, an anti-cancer effect of Compound A which is a novel PARP/Tankyrase simultaneous inhibitor and the genotype of the p53 gene through an in vitro cell base assay in the same experimental method as Example 1 in 18 human colon cancer cell lines.

Experiment Result

As a result of the comparison with the $IC_{50}$ of Compound A, which is a PARP/Tankyrase simultaneous inhibitor, and the p53 genotype commonly found in colon cancer in 18 human colon cancer cell lines, colon cancer cells with the normal p53 genotype were analyzed with low $IC_{50}$ values. The relationship between the p53 genotype and Compound A, a novel PARP/Tankyrase simultaneous inhibitor, was shown.

TABLE 2

| p53 Wild-type cell line | $IC_{50}$ (μM) Compound A | p53 Mutant type cell line | $IC_{50}$ (μM) Compound A |
|---|---|---|---|
| LS174T | 12.19 | Colo320HSR | 8.267 |
|  |  | HT29 | 32.21 |
| RKO | 12.3 | Caco-2 | 19.24 |
|  |  | Colo205 | 24.45 |
| HCT116 | 13.18 | Colo201 | 28.43 |
|  |  | DLD-1 | 85.57 |
| LoVo | 18.57 | SW620 | 96.65 |
|  |  | HCT-15 | >100 |
| HCT8 | 39.5 | LS1034 | >100 |
|  |  | KM12C | >100 |
| SW48 | >100 | SW1417 | >100 |
|  |  | SW480 | >100 |

Example 3: Anticancer Susceptibility Genotype Analysis of Compound A

In order to analyze the degree of apoptosis of Compound A, which is a novel PARP/Tankyrase simultaneous inhibitor, depending on the presence or absence of the p53 gene and the presence or absence of the DNA repair gene, the present inventors reduced gene expression by an ATR, XLF, XRCC4 and LIG4 siRNA knockdown method known as a DNA repair gene in the human colon cancer cell line HCT116 in which the p53 normal gene is present, and then treated with Compound A, which is a novel PARP/Tankyrase simultaneous inhibitor. Then, the number of cells was measured by trypan blue staining assay to confirm the degree of apoptosis. As the experimental conditions and methods, the HCT116 p53 null human colon cancer cell line in which the p53 gene is normal and the HCT116 and p53 gene are deficient is cultured in RPMI1640 (10% FBS, 1% penicillin/streptomycin), and $1\times10^5$ per well was cultured at 37° C. for 24 hours in a 60 mm plate. ATR, XLF, XRCC4 and LIG4 (SEQ ID NO: 4; ATR siRNA 5'-GAGUUCUCAGAAGU-CAACC-3', SEQ ID NO: 5; XLF siRNA 5'-CGCUGAUUC-GAGAUCGAUUGA-3', SEQ ID NO: 6; XRCC4 siRNA 5'-CUGAUCUCUCUGGGUUGGCUU-3', SEQ ID NO: 7; LIG4 siRNA 5'-GGGAGUGUCUCAUGUAAUA-3') were infused into cells by means of Lipofectamin 2000 (Invitrogen), and knocked down at 37° C. for 48 hours. The cells were treated with 25 µM and 50 µM of Compound A, which is a novel PARP/Tankyrase simultaneous inhibitor. After 48 hours of culturing, the number of cells was measured by trypan blue staining and the degree of apoptosis was confirmed.

Experiment Result

DNA repair-related genes were knocked down according to the presence or absence of p53 gene in HCT116 and p53-deficient HCT116 (HCT116 p53 null), which are colon cancer cell lines of normal genotype p53. As a result of analyzing a DNA repair gene which shows the susceptibility only in Compound A, which is a novel PARP/Tankyrase simultaneous inhibitor, in case where the p53 gene is normal and the LIG gene is deficient, the apoptosis is significantly increased, thus showing a selective result in Compound A, which is a novel PARP/Tankyrase simultaneous inhibitor (FIG. 1).

Example 4: Analysis of LIG4 Genotype in Colon Cancer Cells

In order to confirm an LIG4 genotype in the colon cancer cell line, the present inventors analyzed the mutation/deficiency of an LIG4 genotype in 20 colon cancer cell lines through RT-PCR and sequencing. The conditions and methods of the experiment were as follows: A total of 20 colon cancer cell lines were subjected to total RNA extraction with Trizol RNA extraction method using a homogenizer, and 500 ng of total RNA was re-synthesized into cDNA and PCR was performed using LIG4 primer (SEQ ID NO: 8; LIG4 primer Exon2-1 forward primer 5'-GCTAGCTGCTATT-GCAGATATTGAGC-3', SEQ ID NO: 9; LIG4 primer Exon2-1 reverse primer 5'-AGAACCTTCAGTAGGA-GAAGCACCAA-3', SEQ ID NO: 10; LIG4 primer Exon2-2 forward primer Exon2-2 forward primer 5'-CCTGGT-GAGAAGCCATCTGT-3', SEQ ID NO: 11; LIG4 primer Exon2-2 reverse primer 5'-GCCTTCCCCCTAAGTT-GTTC-3'). After electrophoresis on 1% agarose gel, the mutant analysis was confirmed by sanger sequencing of the PCR product in which the expression of LIG4 was confirmed through Et-Br staining.

Experiment Result

In order to confirm whether there is any mutation of LIG4 genotype in 20 human colon cancer cell lines, the G833 and T1704 sites, which are known as malfunction mutation sites of the LIG4 gene, were analyzed by the singer sequencing method. As a result, it has been confirmed that there is a mutation of LIG4 genotype in 8 colon cancer cell lines among 20 thereof.

TABLE 3

| Colon cancer cells | | SW460 | SW620 | HCT116 | HT29 | RKO | DLO1 | SW1417 | Colo320HSR |
|---|---|---|---|---|---|---|---|---|---|
| LIG4 mutation | 833G>A | WT | WT | WT | WT | WT | WT | WT | WT |
| (DNA ligase4) | 1704T>C | WT | WT | WT | WT | Mut | WT | WT | Mut |

| Colon cancer cells | | Ls174T | HCT8 | L91034 | Colo201 | LOVO | SNUC2A | KM12C | HCT15 |
|---|---|---|---|---|---|---|---|---|---|
| LIG4 mutation | 833G>A | Mut | WT | WT | WT | Mut | WT | WT | Mut |
| (DNA ligase4) | 1704T>C | WT | WT | WT | WT | WT | WT | Mut | Mut |

| Colon cancer cells | | CaCO2 | KM12CL4 | Colo205 | SW48 |
|---|---|---|---|---|---|
| LIG4 mutation | 833G>A | Mut | WT | WT | WT |
| (DNA ligase4) | 1704T>C | WT | Mut | WT | WT |

Example 5: Analysis of Apoptosis According to p53 and LIG4 Genotypes

In order to analyze the degree of apoptosis of Compound A, which is a novel PARP/Tankyrase simultaneous inhibitor according to a p53 genotype and LIG4 genotype, the present inventors treated a novel PARP/Tankyrase simultaneous inhibitor, Compound A, and a competitive drug PARP inhibitor, olaparib, in RKO, LoVo human colon cancer cell line in which the p53 gene is a normal type and the LIG4 gene is a mutant type and an SW620 human colon cancer cell line in which the p53 gene is a mutant type and the LIG4 gene is a normal type. The number of cells was measured by trypan blue staining assay to confirm the degree of apoptosis. The conditions and methods of the experiment were as follows: RKO, LoVo human colon cancer cell line in which the p53 gene is a normal type and the LIG4 gene is a mutant type and the SW620 human colon cancer cell line in which the p53 gene is a mutant type and the LIG4 gene is a normal type were cultured in RPMI1640 (10% FBS, 1% penicillin/streptomycin) and cultured in a 60 mm plate at $1\times10^5$ per well for 24 hours at 37° C. Compound A, which is a novel PARP/Tankyrase simultaneous inhibitor, and olaparib, which is a competitive drug PARP inhibitor, were treated with each of 25 µM and 50 µM and were cultured for 48 hours. The number of cells was measured by trypan blue staining assay to confirm the degree of apoptosis.

Experiment Result

Figure 2:
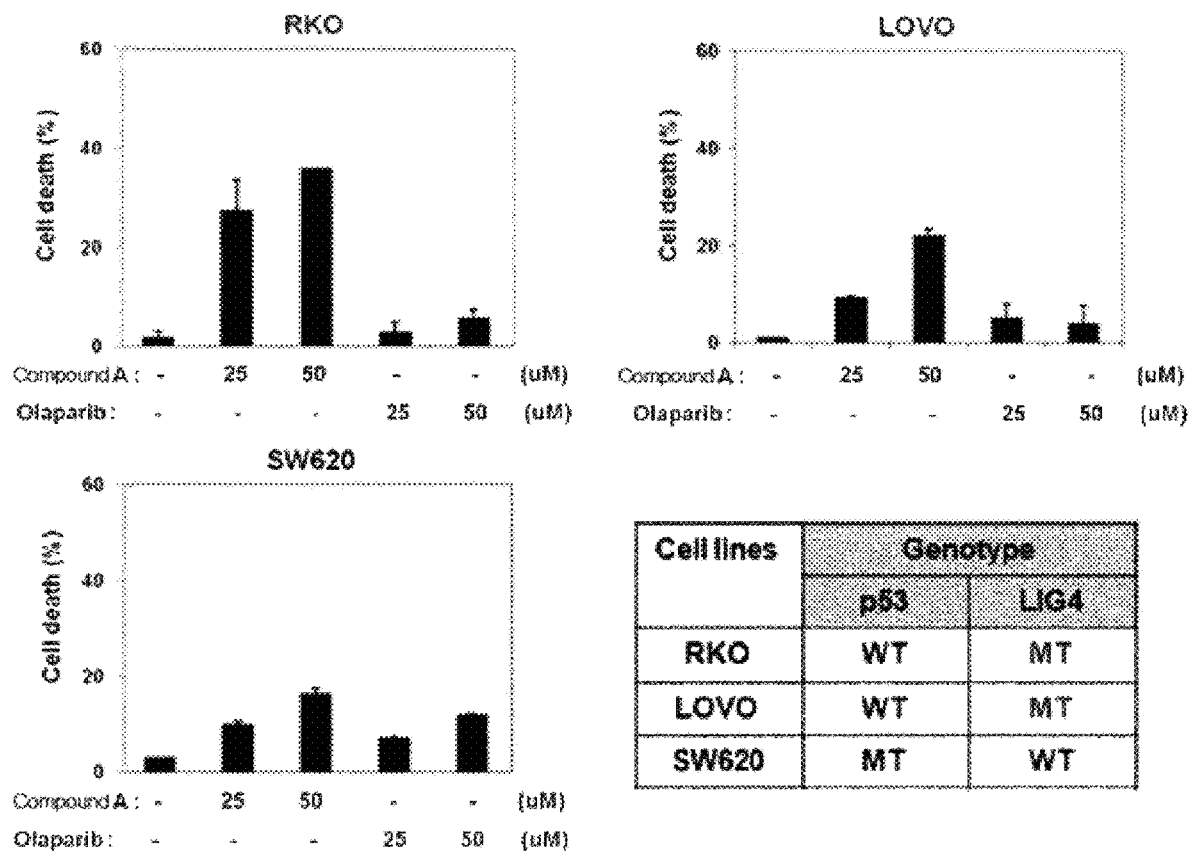
FIG. 2 illustrates the results of apoptosis analysis for the treatments of Compound A and olaparib, which are simultaneous inhibitors against PARP/Tankyrase, according to a p53 genotype and an LIG4 genotype in various human colon cancer cell lines (RKO, LoVo and SW620).

As a result of observing the degree of apoptosis by treating Compound A, which is a novel PARP/Tankyrase simultaneous inhibitor, and olaparib, which is a competitive drug PARP inhibitor in a human colon cancer cell line whose p53 and LIG4 genotypes are difference, the apoptosis was induced by Compound A, which is a novel PARP/Tankyrase simultaneous inhibitor, in the RKO, LoVo human colon cancer cell line in which the p53 gene is a normal type and an LIG4 gene is a mutant type, and no apoptosis effect was shown in olaparib, which is a competitive drug PARP inhibitor. In the SW620 human colon cancer cell line in which the p53 gene is a mutant type and an LIG4 gene is a normal type, it was observed that both Compound A, which is a novel PARP/Tankyrase simultaneous inhibitor, and olaparib showed low apoptosis effect, thus showing a selective result in Compound A, which is a novel PARP/Tankyrase simultaneous inhibitor in which the p53 genotype is normal and an LIG4 genotype is a mutant type (FIG. 2).

Example 6: DNA Damage Analysis of p53 Genotype Normal Type Cells

In order to analyze the degree of DNA damage of Compound A, which is a novel PARP/Tankyrase simultaneous inhibitor when the p53 gene is a normal type, the present inventors treated a novel PARP/Tankyrase simultaneous inhibitor, Compound A, and the competitive drug PARP inhibitor, olaparib, in the HCT116 human colon cancer cell line in which the p53 gene is a normal type, and then the DNA damage was confirmed by immunochemical method as the expression level of r-H2AX. The conditions and methods of the experiment were as follows: HCT116 human colon cancer cell line in which the p53 gene is a normal type was cultured in RPMI1640 (10% FBS, 1% penicillin/streptomycin) and cultured in a 60 mm plate at $1 \times 10^5$ per well for 24 hours at 37° C. Compound A, which is a novel PARP/Tankyrase simultaneous inhibitor, and olaparib, which is a competitive drug PARP inhibitor, were treated with 50 μM each and were cultured for 48 hours. After being fixed with 4% paraformaldehyde for 15 minutes at room temperature and being washed with TBS-T buffer three times for 10 minutes, they were permeabilized with 0.5% Triton X-100 for 10 minutes. After being washed three times for 10 minutes with TBS-T buffer, they were blocked with 5% BSA for 1 hour at room temperature. The r-H2AX antibody was diluted at a ratio of 1:100 in 1% BSA, reacted overnight at 4° C., washed three times for 10 minutes with TBS-T buffer, and the secondary antibody (alexa Fluor®488 fitc) was diluted at a ratio of 1:100 in 1% BSA, reacted at room temperature for 2 hours, and then washed with TBS-T A buffer three times for 10 minutes, and stained with DAPI (4',6-diamidino-2-phenylindole) to confirm the expression level of r-H2AX under a fluorescence microscope.

Experiment Result

Figure 3:
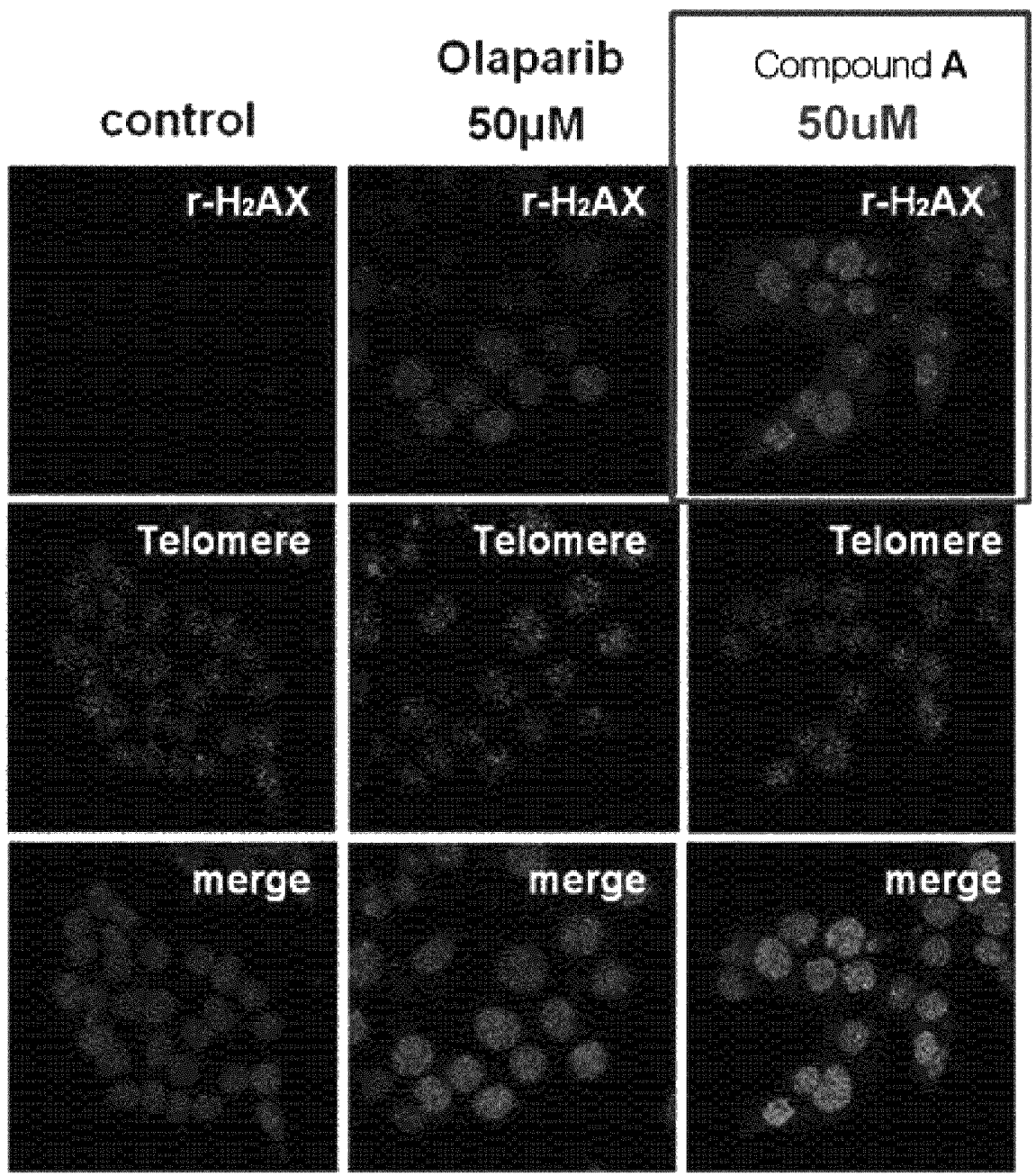
FIG. 3 illustrates the results of analysis of DNA damage for the treatments of Compound A and olaparib, which are simultaneous inhibitors against PARP/Tankyrase, in the human colon cancer cell line HCT116 in which the p53 genotype and the LIG4 genotype are normal type, through immunochemical methods.

As a result of observing the DNA damage with the expression level of r-H2AX by imuunocytochemistry method by treating Compound A, which is a novel PARP/Tankyrase simultaneous inhibitor, and olaparib, which is a competitive drug PARP inhibitor in a human colon cancer cell lineHCT116 in which the p53 gene is a normal type, a group treated with Compound A, the novel PARP/Tankyrase simultaneous inhibitor, showed a higher expression of r-H2AX than the group treated with olaparib, thus inducing DNA damage of Compound A, which is a novel PARP/Tankyrase simultaneous inhibitor (FIG. 3).

Example 7: DNA Damage Analysis of p53 Genotype and LIG4 Genotype Mutant Cells

In order to analyze the degree of DNA damage of Compound A, which is a novel PARP/Tankyrase simultaneous inhibitor, when the p53 gene is a normal type and the LIG4 gene is a mutant type, the present inventors treated a novel PARP/Tankyrase simultaneous inhibitor, Compound A, and the competitive drug PARP inhibitor, olaparib, in the RKO human colon cancer cell line in which the p53 gene is a normal type and the LIG4 gene is a mutant type, and the DNA damage was confirmed by the immunochemical method as the expression level of r-H2AX. The conditions and methods of the experiment were as follows: RKO human colon cancer cell line in which the p53 gene is a normal type and the LIG4 gene is a mutant type was cultured in RPMI1640 (10% FBS, 1% penicillin/streptomycin) and cultured in a 60 mm plate at $1 \times 10^5$ per well for 24 hours at 37° C. Compound A, which is a novel PARP/Tankyrase simultaneous inhibitor, and olaparib, which is a competitive drug PARP inhibitor, were treated with 50 μM each and were cultured for 48 hours. After being fixed with 4% paraformaldehyde for 15 minutes at room temperature and being washed with TBS-T buffer ten times for 5 minutes, they were permeabilized with 0.5% Triton X-100 for 10 minutes. After being washed three times for 10 minutes with TBS-T buffer, they were blocked with 5% BSA for 1 hour at room temperature. The r-H2AX antibody was diluted at a ratio of 1:100 in 1% BSA, reacted overnight at 4° C., washed three times for 10 minutes with TBS-T buffer, and the secondary antibody (Alexa Fluor®488 fitc) was diluted at a ratio of 1:100 in 1% BSA, reacted at room temperature for 2 hours, and then washed with TBS-T A buffer three times for 10 minutes, and stained with DAPI to confirm the expression level of r-H2AX under a fluorescence microscope.

Experiment Result

Figure 4:
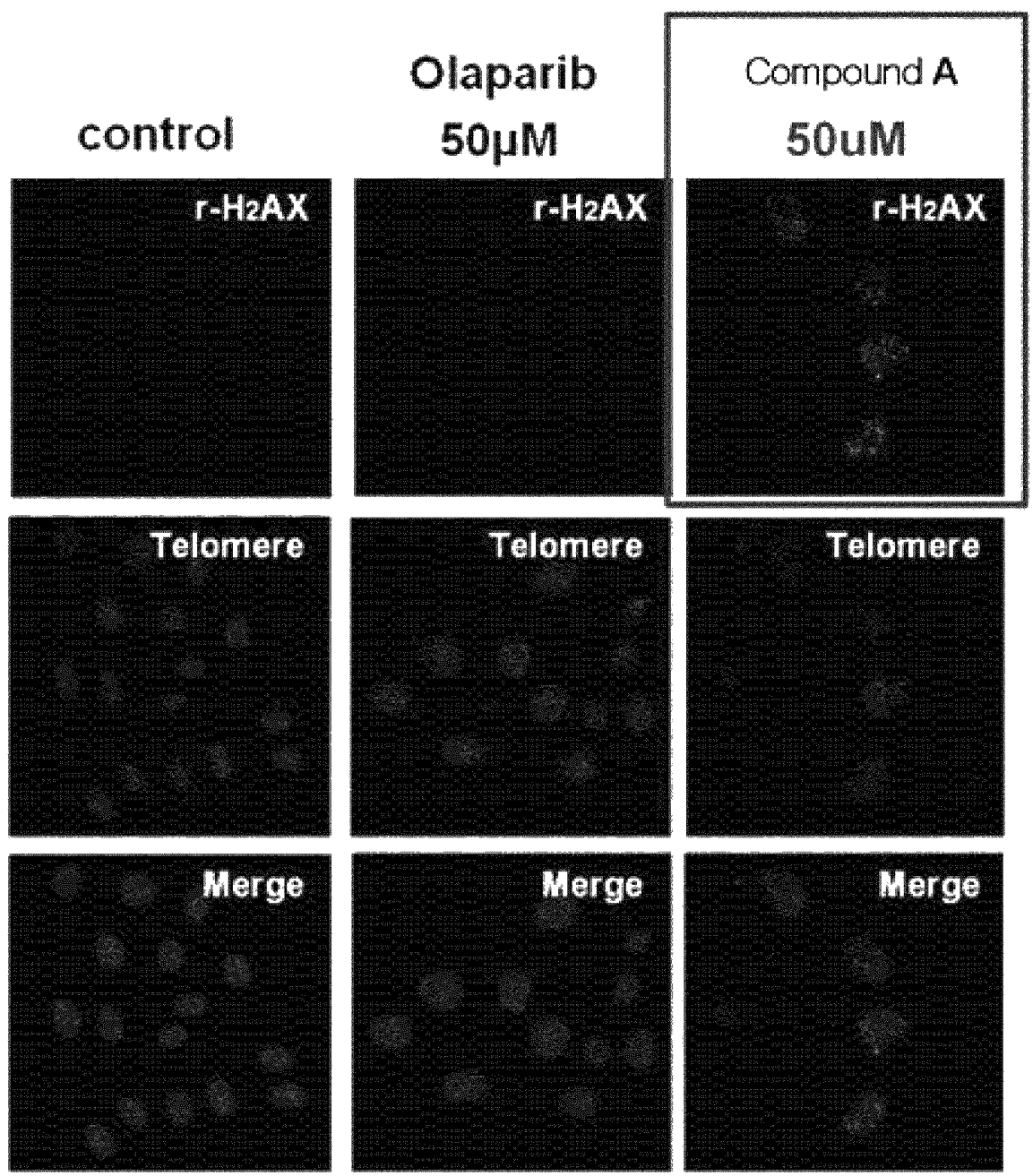
FIG. 4 illustrates the results of analysis of DNA damage for the treatments of Compound A and olaparib, which are simultaneous inhibitors against PARP/Tankyrase, in the human colon cancer cell line RKO in which the p53 genotype is a normal type and an LIG4 genotype is a mutant type, through immunochemical methods.

As a result of observing the DNA damage with the expression level of r-H2AX by imuunocytochemistry method by treating Compound A, which is a novel PARP/Tankyrase simultaneous inhibitor, and olaparib, which is a competitive drug PARP inhibitor in the RKO human colon cancer cell line in which the p53 gene is a normal type and the LIG4 gene is a mutant type, the expression of r-H2AX was increased only in the group treated with Compound A, which is a novel PARP/Tankyrase simultaneous inhibitor, indicating that it induces DNA damage of Compound A, which is a novel PARP/Tankyrase simultaneous inhibitor (FIG. 4).

Example 8: DNA Damage and Apoptosis Analysis of p53 Genotype Normal Type and LIG4 Genotype Mutant Type Cells In order to analyze the degree of DNA damage and the degree of apoptosis of Compound A, which is a novel PARP/Tankyrase simultaneous inhibitor, when the p53 gene is a normal type and the LIG4 gene is a mutant type, the present inventors treated a novel PARP/Tankyrase simultaneous inhibitor, Compound A, and the competitive drug PARP inhibitor; olaparib, in the HCT116 human colon cancer cell line in which the p53 gene and an LIG4 gene are normal types and in the RKO human colon cancer cell line in which the p53 gene is a normal type and an LIG4 gene is a mutant type, and then confirmed the DNA damage with the expression level of r-H2Ax by western blotting method and confirmed the degree of apoptosis with the expression level of cleaved caspase 3. The conditions and method of the experiment were as follows: The HCT116 human colon cancer cell line in which the p53 gene and an LIG4 gene are normal types and the RKO human colon cancer cell line in which the p53 gene is a normal type and an LIG4 gene is a mutant type were cultured in RPMI1640 (10% FBS, 1% penicillin/streptomycin) and cultured in a 60 mm plate at $1\times10^5$ per well for 24 hours at 37° C. Compound A, which is a novel PARP/Tankyrase simultaneous inhibitor, and olaparib, which is a competitive drug PARP inhibitor, were treated with 50 μM each and were cultured for 48 hours. Then, the cells were obtained using a centrifuge. Each cell thus obtained was dissolved using an RIPA buffer, and the proteins were extracted using a high-speed centrifuge. 30 μg protein per cell was electrophoresed by western blot method to separate proteins and transferred to PDVF membrane. The r-H2AX, truncated caspase 3, and b-actin antibody were diluted with each 1:2000 in 5% skim milk. Then, the cells were reacted at 4° C. for 12 hours and then washed three times for 15 minutes with TBS-T buffer. The secondary antibody was diluted with each 1:2000 ratio in 5% skim milk and reacted at room temperature for 2 hours. It was washed with TBS-T buffer three times for 15 minutes to induce luminescence of PDVF membrane using ECL (Enhanced Chemiluminescence) buffer solution to develop protein expression on each anti-body using an X-ray film.

Experiment Result

Figure 5A:
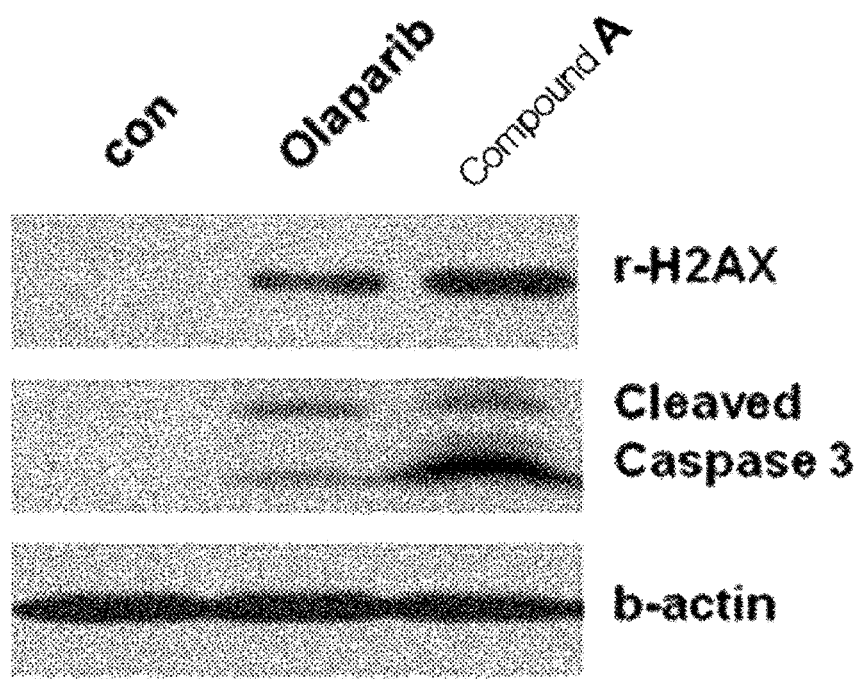
FIGS. 5A and 5B illustrate DNA damage and apoptosis for the treatments of Compound A and olaparib, which are simultaneous inhibitors against PARP/Tankyrase, in human colon cancer cell lines HCT116 and RKO through Western blot.
Figure 5B:
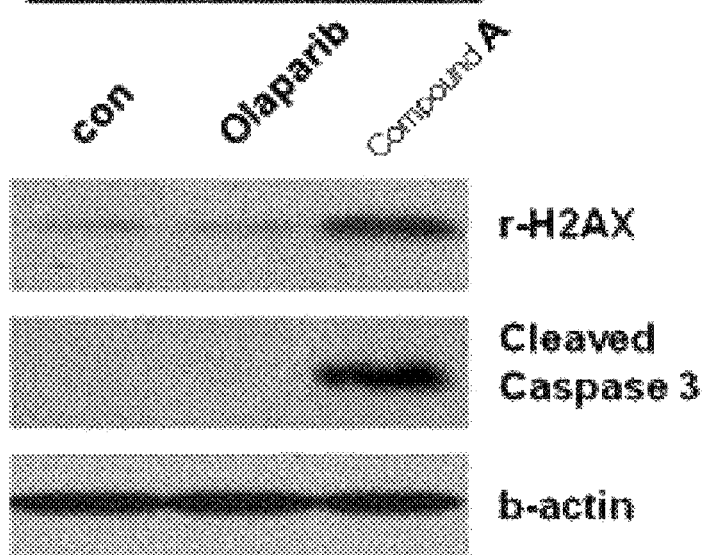

As a result of observing the degree of DNA damage and apoptosis with the expression levels of r-H2AX and truncated caspase 3 by western blotting by treating Compound A, which is a novel PARP/Tankyrase simultaneous inhibitor, and olaparib, which is a competitive drug PARP inhibitor, in the human colon cancer cell line HCT116 in which the p53 genotype is a normal type and the human colon cancer cell line RKO in which an LIG4 genotype is a mutant type, the group treated with Compound A, which is a novel PARP/Tankyrase simultaneous inhibitor, showed an increased expression of r-H2AX than the group treated with olaparib, and showed an increased expression amount of the truncated caspase 3, thus inducing DNA damage of Compound A, which is a novel PARP/Tankyrase simultaneous inhibitor, and apoptosis (FIG. 5).

Example 9: Analysis of Apoptosis in the Case where an LIG4 Genotype is a Mutant Type Cell in a Cell Line where the p53 Genotype is a Normal Type In order to analyze the degree of apoptosis of Compound A, which is a novel PARP/Tankyrase simultaneous inhibitor, when the p53 genotype is a normal type and an LIG4 genotype is a mutant type, the present inventors treated a novel PARP/Tankyrase simultaneous inhibitor, Compound A, and the competitive drug PARP inhibitor, olaparib, while overexpressing an LIG4 mutant type in the HCT8 human colon cancer cell line in which the p53 gene is a normal type and an LIG4 genotype is a normal type. Then, the number of cells was measured by trypan blue staining assay to confirm the degree of apoptosis. The conditions and methods of the above experiment were as follows: HCT8 human colon cancer cell line in which the p53 gene is a normal type and the LIG4 gene is a normal type was cultured in RPMI1640 (10% FBS, 1% penicillin/streptomycin) and cultured in a 60 mm plate at $1\times10^5$ per well for 24 hours at 37° C. G833A or T1704C plasmid DNA in which an LIG4 genotype is a mutant type was infused into cells by means of Lipofectamin 2000 (Invitrogen), and then overexpressed at 37° C. for 48 hours. Then, the cells were treated with each of 25 μM and 50 μM of Compound A, which is a novel PARP/Tankyrase simultaneous inhibitor and olaparib, a competitive drug PARP inhibitor. After 48 hours of culturing, the number of cells was measured by trypan blue staining and the degree of apoptosis was confirmed.

Experiment Result

Figure 6:
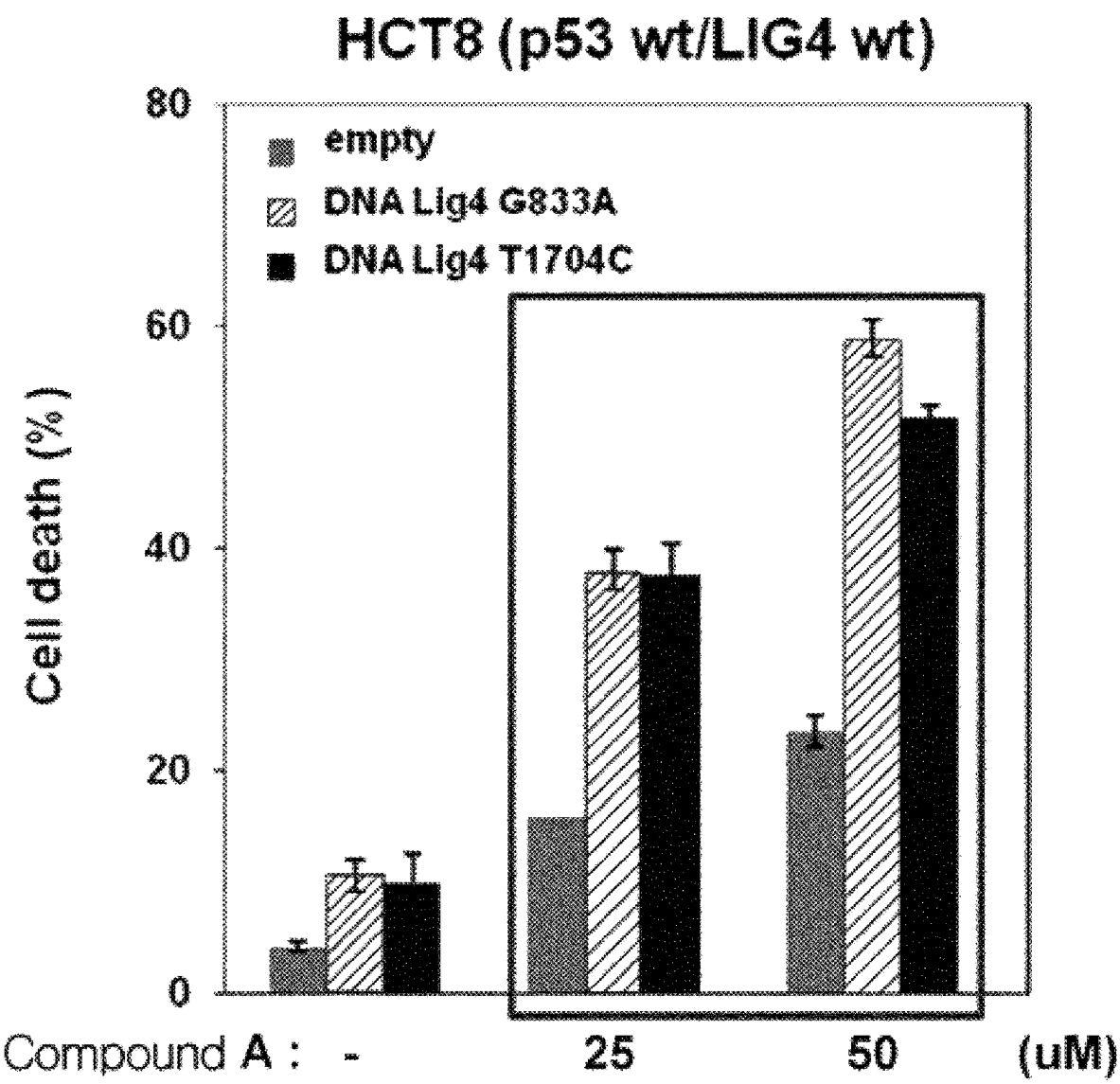
FIG. 6 illustrates the results of apoptosis analysis for the treatment of Compound A, which is a simultaneous inhibitor against PARP/Tankyrase, after overexpressing mutant type LIG4 (G833A or T1704C) in human colon cancer cell line HCT8 (p53 WT/LIG4 WT).

As a result of observing the degree of apoptosis by trypan blue straining exclusion assay by treating Compound A, which is a novel PARP/Tankyrase simultaneous inhibitor while expressing G833A or T1704C in which an LIG4 genotype is a mutant type in the human colon cancer cell line HCT8 in which the p53 genotype and an LIG4 genotype is a normal type, as compared to a control group (empty) into which an LIG4 mutant gene is not inserted, in case where an LIG4 mutant G833A or T1704C is overexpressed, it showed that the apoptosis was increased by Compound A, which is a novel PARP/Tankyrase simultaneous inhibitor (FIG. 6).

Example 10: Analysis of Apoptosis in the Case of LIG4 Genotype Mutant Cells in a Cell Line in which the p53 Genotype is a Mutant Type In order to analyze the degree of apoptosis of Compound A, which is a novel PARP/Tankyrase simultaneous inhibitor, when the p53 genotype is a mutant type and an LIG4 genotype is a mutant type, the present inventors treated a novel PARP/Tankyrase simultaneous inhibitor, Compound A, and the competitive drug PARP inhibitor, olaparib, while overexpressing an LIG4 mutant type in the SW620 human colon cancer cell line in which the p53 gene is a mutant type and an LIG4 genotype is a normal type. Then, the number of cells was measured by trypan blue staining assay to confirm the degree of apoptosis. The conditions and methods of the above experiment were as follows: SW620 human colon cancer cell line in which the p53 gene is a mutant type and the LIG4 gene is a normal type was cultured in RPMI1640 (10% FBS, 1% penicillin/streptomycin) and cultured in a 60 mm plate at $1\times10^5$ per well for 24 hours at 37° C. G833A or T1704C plasmid DNA in which an LIG4 genotype is a mutant type was infused into cells by means of Lipofectamin 2000 (Invitrogen), and then overexpressed at 37° C. for 48 hours. Then, the cells were treated with each of 25 μM and 50 μM of Compound A, which is a novel PARP/Tankyrase simultaneous inhibitor and olaparib, a competitive drug PARP inhibitor. After 48 hours of culturing, the number of cells was measured by trypan blue staining and the degree of apoptosis was confirmed.

Experiment Result

Figure 7:
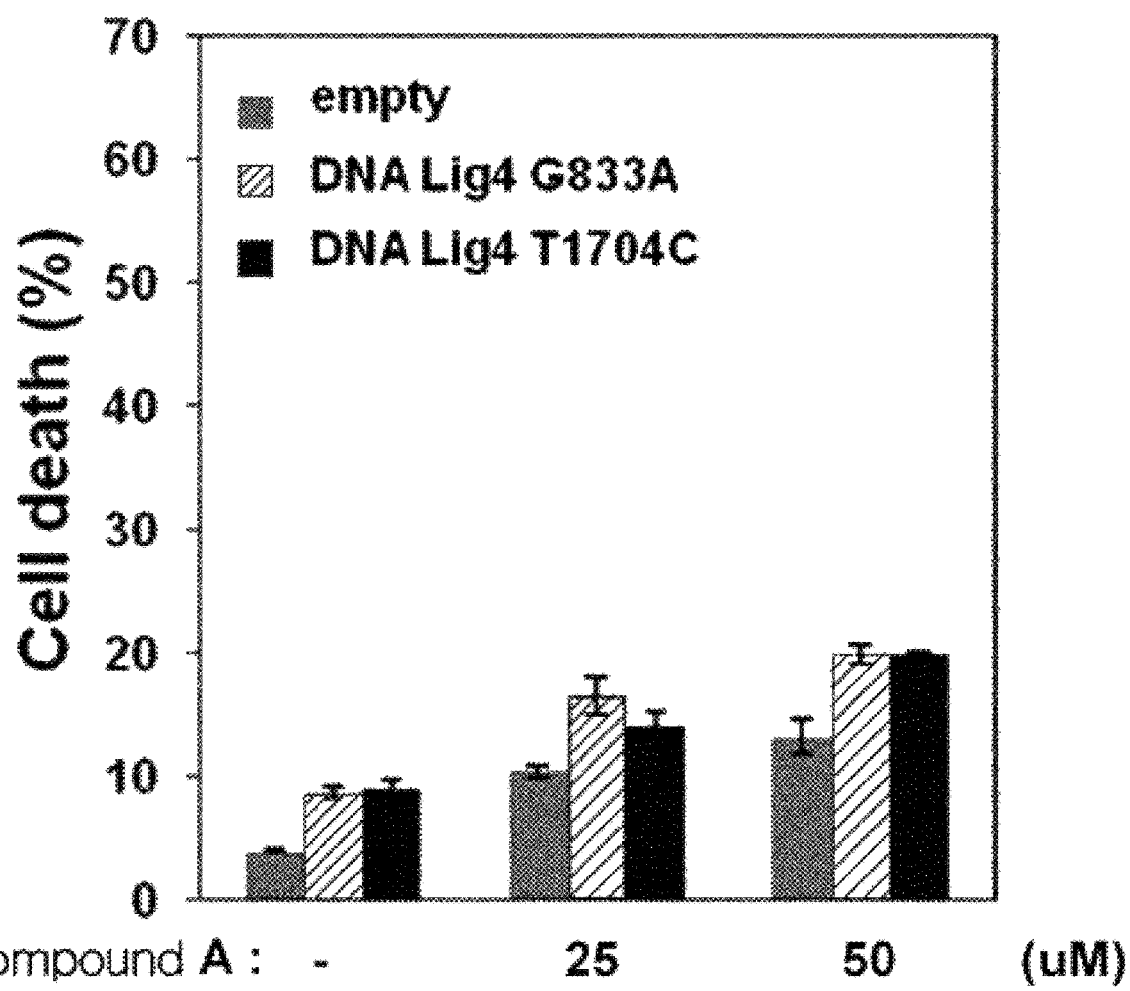
FIG. 7 illustrates the results of apoptosis analysis for the treatment of Compound A, which is a simultaneous inhibitor against PARP/Tankyrase, overexpressing mutant type LIG4 (G833A or T1704C) in human colon cancer cell line SW620 (p53 MT/LIG4 WT).

As a result of observing the degree of apoptosis by trypan blue straining exclusion assay by treating Compound A, which is a novel PARP/Tankyrase simultaneous inhibitor while expressing G833A or T1704C in which an LIG4 genotype is a mutant type in the human colon cancer cell line SW620 in which the p53 genotype is a mutant type and an LIG4 genotype is a normal type, as compared to a control group (empty) into which an LIG4 mutant gene is not inserted, in case where an LIG4 mutant G833A or T1704C is overexpressed, no change in the apoptosis was shown by Compound A, which is a novel PARP/Tankyrase simultaneous inhibitor. As illustrated in FIG. 5, only in case where the p53 genotype is a normal type, the apoptosis was induced by Compound A, which is a novel PARP/Tankyrase simultaneous inhibitor for an LIG4 mutant (FIG. 7).

Example 11: Analysis of DNA Damage and Apoptosis in LIG4 Genotype Mutant Cells in the Cell Line in which the p53 Genotype is a Normal Type The present inventors conducted an experiment in the same manner as Example 9 to analyze the degree of apoptosis and DNA damage of Compound A, which is a novel PARP/Tankyrase simultaneous inhibitor, when the p53 genotype is a mutant type and an LIG4 genotype is a mutant type. The number of cells was measured by trypan blue staining method and the degree of apoptosis was confirmed. The cells were obtained using a centrifuge. Each cell thus obtained was dissolved using an RIPA buffer, and the proteins were extracted using a high-speed centrifuge. 30 μg protein per cell was electrophoresed by western blot method to separate proteins and transferred to PDVF membrane. The r-H2AX, truncated caspase 3, and b-actin antibody were diluted with each 1:2000 ratio in 5% skim milk. Then, the cells were reacted at 4° C. for 12 hours and then washed three times for 15 minutes with TBS-T buffer. The secondary antibody was diluted with each 1:2000 ratio in 5% skim milk and reacted at room temperature for 2 hours. It was washed with TBS-T buffer three times for 15 minutes to induce luminescence of PDVF membrane using ECL buffer solution to develop protein expression on each anti-body using an X-ray film.

Experiment Result

Figure 8A:
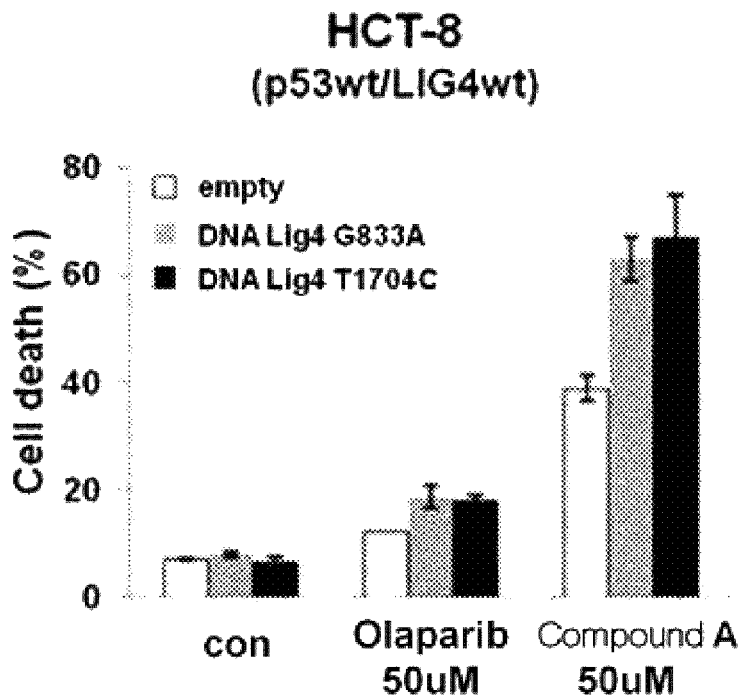
FIGS. 8A and 8B illustrate the results of analysis of DNA damage and apoptosis for the treatments of Compound A and olaparib, which are simultaneous inhibitors against PARP/Tankyrase, after overexpressing mutant type LIG4 (G833A or T1704C) in human colon cancer cell line HCT8 (p53 WT/LIG4 WT).
Figure 8B:
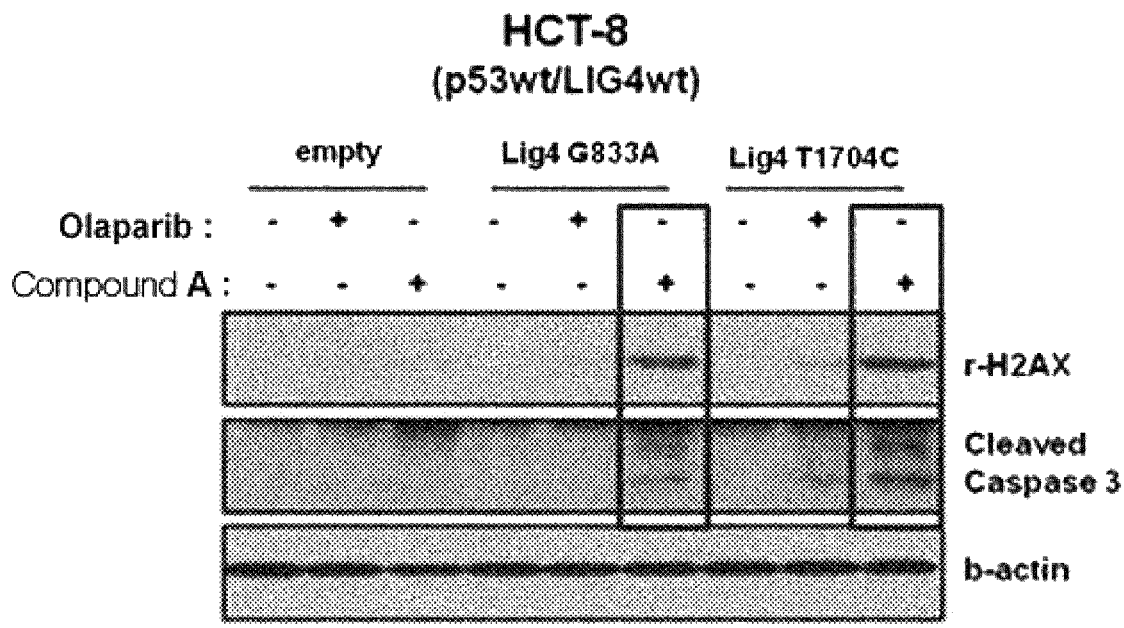

As a result of observing the degree of DNA damage and the degree of apoptosis by r-H2AX and the expression level of truncated caspase 3 by western blot and observing the degree of apoptosis by trypan blue straining exclusion assay by treating Compound A, which is a novel PARP/Tankyrase simultaneous inhibitor and olaparib, which is a competitive drug PARP inhibitor, while overexpressing G833A or T1704C in which an LIG4 genotype is a mutant type in the human colon cancer cell line HCT8 in which the p53 genotype and an LIG4 genotype is a normal type, the group treated with Compound A, which is a novel PARP/Tankyrase simultaneous inhibitor, showed an increased apoptosis by Compound A, which is a novel PARP/Tankyrase simultaneous inhibitor in case of overexpressing the LIG4 mutant G833A or T1704C as compared to a control group (empty) into which an LIG4 mutant gene is not inserted, rather than olaparib, which is a competitive drug (FIG. 8A). The expression of r-H2AX and the expression amount of truncated caspase 3 were also increased, indicating that only when the p53 genotype is a normal type and an LIG4 genotype is a mutant type, the DNA damage and apoptosis of Compound A, which is a novel PARP/Tankyrase simultaneous inhibitor, were induced (FIG. 8B)

Example 12: Analysis of Apoptosis by p53 Mutant Type and LIG4 Normal Type Expression in a Cell Line in which the p53 Genotype is a Normal Type and an LIG4 Genotype is a Mutant Type In order to analyze the degree of apoptosis of Compound A, which is a novel PARP/Tankyrase simultaneous inhibitor according to the expression of mutant type p53 and normal type LIG4 when the p53 genotype is a normal type and an LIG4 genotype is a mutant type, the RKO human colon cancer cell line in which the p53 gene is a normal type and an LIG4 genotype is a mutant type was cultured in the same manner as in Example 7. The p53 mutant type plasmid DNA and the plasmid DNA in which an LIG4 genotype is a normal type were infused into the cells for 48 hours for overexpression at 37° C., and then Compound A, which is a novel PARP/Tankyrase simultaneous inhibitor, and olaparip, which is a competitive drug PARP inhibitor, were treated with 25 μM and 50 μM, respectively, for 48 hours. The number of cells was measured by trypan blue staining assay to confirm the degree of apoptosis.

Experiment Result

Figure 9A:
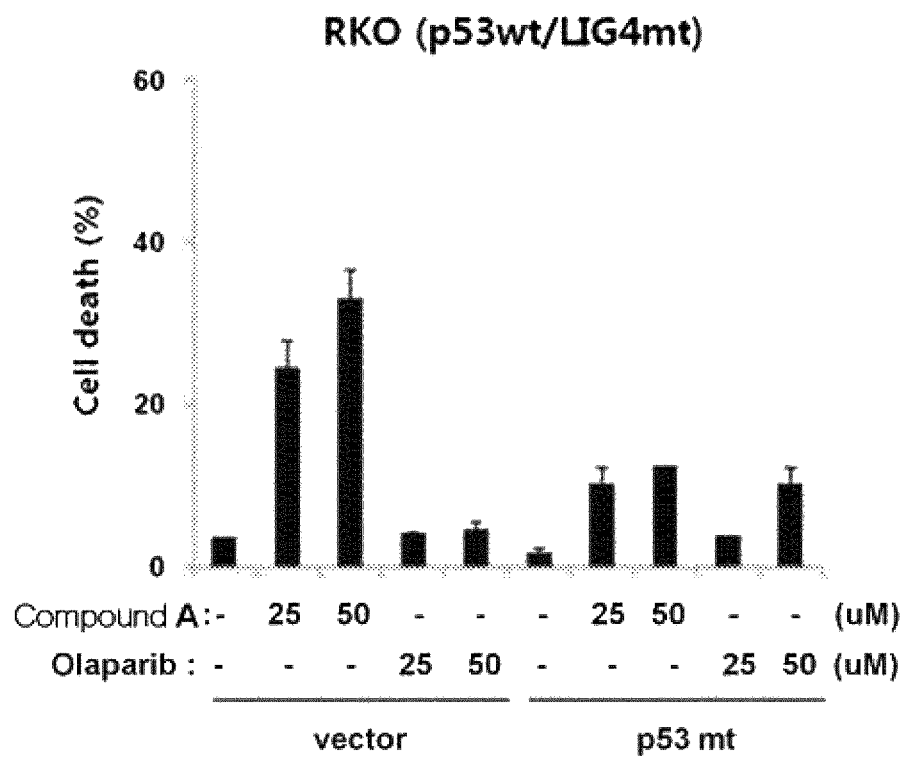
FIGS. 9A and 9B illustrate the results of apoptosis analysis for the treatments of Compound A and olaparib, which are simultaneous inhibitors against PARP/Tankyrase, after overexpressing each of mutant type p53 and normal type LIG4 in human colon cancer cell line RKO (p53 WT/LIG4 MT).
Figure 9B:
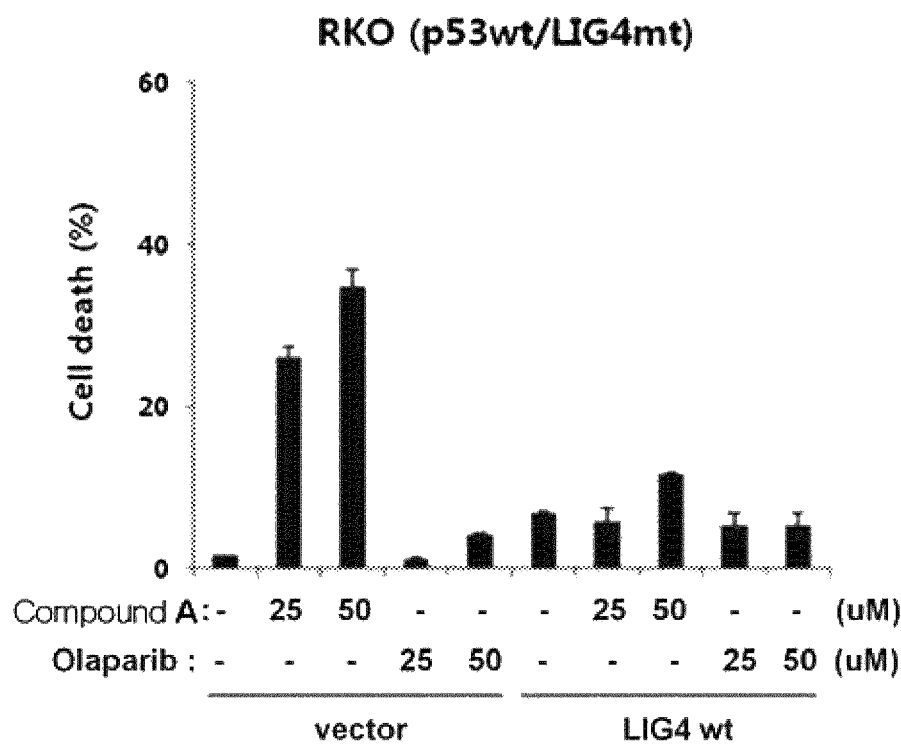
Figure 10A:
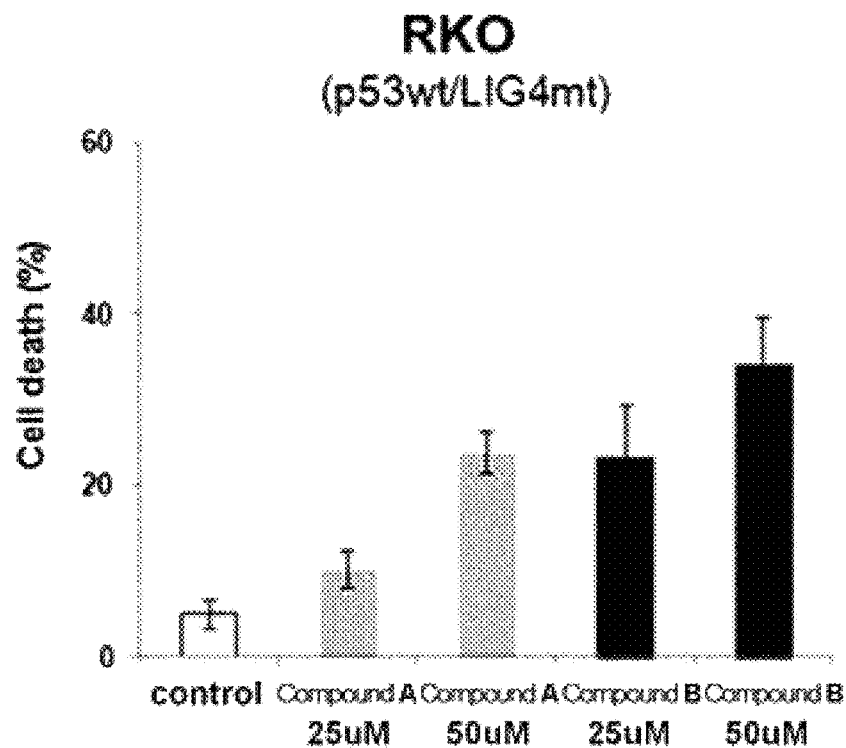
FIGS. 10A and 10B illustrate the results of comparative analysis of the apoptosis for the treatments of Compound A and Compound B, which are the simultaneous inhibitors against PARP/Tankyrase, in the human colon cancer cell line (RKO, LoVo) in which the p53 genotype is the normal type and an LIG4 genotype is the mutant type.
Figure 10B:
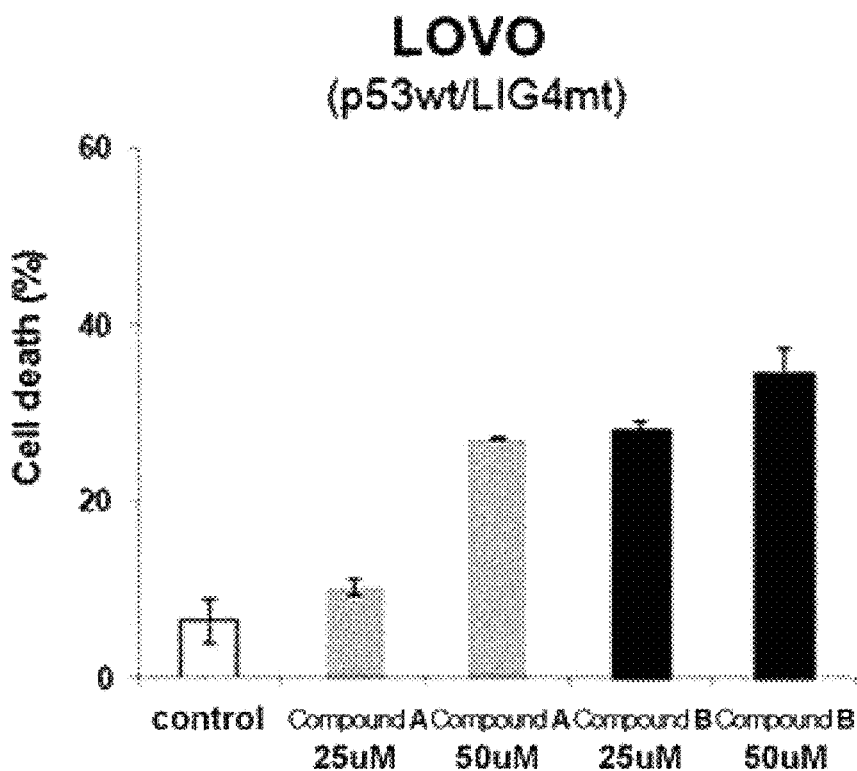

As a result of observing the degree of apoptosis by trypan blue straining exclusion assay by treating Compound A, which is a novel PARP/Tankyrase simultaneous inhibitor, and olaparib, which is a competitive drug PARP inhibitor, while overexpressing the p53 mutant type gene in the human colon cancer cell line RKO in which the p53 genotype is a normal type and an LIG4 genotype is a mutant type, in case where the p53 mutant type gene was overexpressed as compared to a control group (empty) into which the p53 mutant type gene is not inserted, it was observed that the apoptosis was reduced by Compound A, which is a novel PARP/Tankyrase simultaneous inhibitor (FIG. 9A). As a result of observing the degree of apoptosis by trypan blue straining exclusion assay by treating Compound A, which is a novel PARP/Tankyrase simultaneous inhibitor, and olaparib, which is a competitive drug PARP inhibitor, while overexpressing an LIG4 normal type gene in the human colon cancer cell line RKO in which the p53 genotype is a normal type and an LIG4 genotype is a mutant type, in case where an LIG4 normal type gene was overexpressed as compared to a control group (empty) into which an LIG4 normal type gene is not inserted, it was observed that the apoptosis was reduced by Compound A, which is a novel PARP/Tankyrase simultaneous inhibitor (FIG. 9B). When the p53 is a normal type and an LIG4 is a mutant type, the apoptosis of Compound A is the highest (FIG. 9).

Example 13: $IC_{50}$ Analysis of Compound B which is a PARP/Tankyrase Simultaneous Inhibitor According to p53 and LIG4 Genotypes In order to analyze the anticancer activity of Compounds A and B, which are PARP/Tankyrase simultaneous inhibitors, in four types of human colon cancer cell lines of RKO (p53 WT/LIG4 MT), HCT8 (p53 WT, LIG4 WT), SW620 (p53 MT, LIG4 WT), and KM12C (p53 MT, LIG4 MT) with different p53 and LIG4 genotypes, the present inventors measured the cell viability and $IC_{50}$ of cell lines for Compounds A and B, which are PARP/Tankyrase simultaneous inhibitors, through in vitro cell base assay. The conditions and methods of the experiment were as follows: Four types of human colon cancer cell lines were cultured in RPMI1640 (10% FBS, 1% penicillin/streptomycin), and each cell line was cultured in 96 well plate for $2\times10^3$ per well at 37° C. for 24 hours, and the novel PARP/Tankyrase simultaneous inhibitor, Compound A, was diluted by a multiple of 2 at a maximum of 100 μM and a minimum of 0.390625 μM (100 μM, 50 μM, 25 μM, 12.5 μM, 6.25 μM, 3.125 μM, 1.5625 μM, 0.78125 μM and 0.390625 μM). After the treatment, it was cultured at 37° C. for 72 hours. As for the drug treatment group and non-treatment group, the cell viability of each cell line was measured by MTS analysis (Promega, CellTiter 96 AQeous One Solution) and the IC50 of each cell line was measured using the PRISM program.

Experiment Result

As a result of analyzing $IC_{50}$ using MTS analysis of each of the 4 human colon cancer cell lines treated with Compounds A and B, which are novel PARP/Tankyrase simultaneous inhibitors, the lowest $IC_{50}$ values of Compounds A and B was shown in the RKO in which p53 is a normal type and an LIG4 is a mutant type among 4 types of cell lines, indicating that Compounds A and B, which are novel PARP/Tankyrase simultaneous inhibitors, show the most excellent anticancer effect in case where p53 is a normal type and LIG4 is a mutant type (Table 4).

TABLE 4

| Compound Name | Colon cancer cell (IC$_{50}$, uM) | | | |
|---|---|---|---|---|
| | RKO (p53wt/ LIG4mt) | HCT8 (p53wt/ LIG4wt) | SW620 (p53mt/ LIG4wt) | KM12C (p53mt/ LIG4mt) |
| Compound A | 23.71 | 39.5 | 96.65 | >100 |
| Compound B | 12.46 | 62.52 | >100 | >100 |

Example 14: Analysis of Efficacy of Compound A and Compound B According to p53 and LIG4 Genotypes In order to analyze the degree of apoptosis of Compound A, which is a novel PARP/Tankyrase simultaneous inhibitor, according to the p53 genotype and an LIG4 genotype, the present inventors treated Compounds A and B, which are novel PARP/Tankyrase simultaneous inhibitors, in the RKO and LoVo human colon cancer cell lines in which the p53 gene is a normal type and an LIG4 gene is a mutant type. Then, the number of cells was measured by trypan blue staining assay to confirm the degree of apoptosis. The RKO and LoVo human colon cancer cell lines were cultured under the same conditions as in Example 5. Compounds A and B, which are novel PARP/Tankyrase simultaneous inhibitors, were treated with 25 μM and 50 μM, respectively, for 48 hours. After 48 hours of culturing, the number of cells was measured by trypan blue staining assay to confirm the degree of apoptosis.

Experiment Result

As a result of observing the degree of apoptosis by treating each of Compounds A and B, which are novel PARP/Tankyrase simultaneous inhibitors, in the human colon cancer cell lines RKO and LoVo in which the p53 gene is a normal type and an LIG4 gene is a mutant type, in the RKO and LoVo cell lines in which the p53 gene is a normal type and an LIG4 gene is a mutant type, it is shown that the apoptosis effect is high by virtue of Compound B as compared to Compound A, which is a novel PARP/Tankyrase simultaneous inhibitor. In case where the p53 genotype is normal and an LIG4 genotype is a mutant type, Compound B, which is a novel PARP/Tankyrase simultaneous inhibitor, showed a selective result as compared to Compound A.

Example 15: Analysis of Apoptosis of Compound A and Compound B in Cell Lines Different in p53 Genotype and LIG4 Genotype In order to analyze the degree of apoptosis of Compounds A and B, which are novel PARP/Tankyrase simultaneous inhibitors, in a cell line RKO in which the p53 genotype is a normal type and an LIG4 genotype is a mutant type, a cell line SW620 in which the p53 genotype is a mutant type and an LIG4 genotype is a normal type, a cell line HCT8 in which the p53 genotype and an LIG4 genotype are normal, and a cell line KM12C in which the p53 genotype and an LIG4 genotype are mutant, the human colon cancer cell lines of RKO, HCT, SW620 and KM12C with different p53 genotype and LIG4 genotype were cultured in RPMI1640 (10% FBS, 1% penicillin/streptomycin) and cultured in a 60 mm plate at 1×10⁵ per well for 24 hours at 37° C. Compounds A and B, which are novel PARP/Tankyrase simultaneous inhibitors, and olaparib, which is a competitive drug PARP inhibitor, and NVP-TNKS656, which is a Tankyrase inhibitor, were treated with each of 25 μM and 50 μM. After 48 hours of culturing, the number of cells was measured by trypan blue staining assay to confirm the degree of apoptosis.

Experiment Result

Figures 11A, 11B:
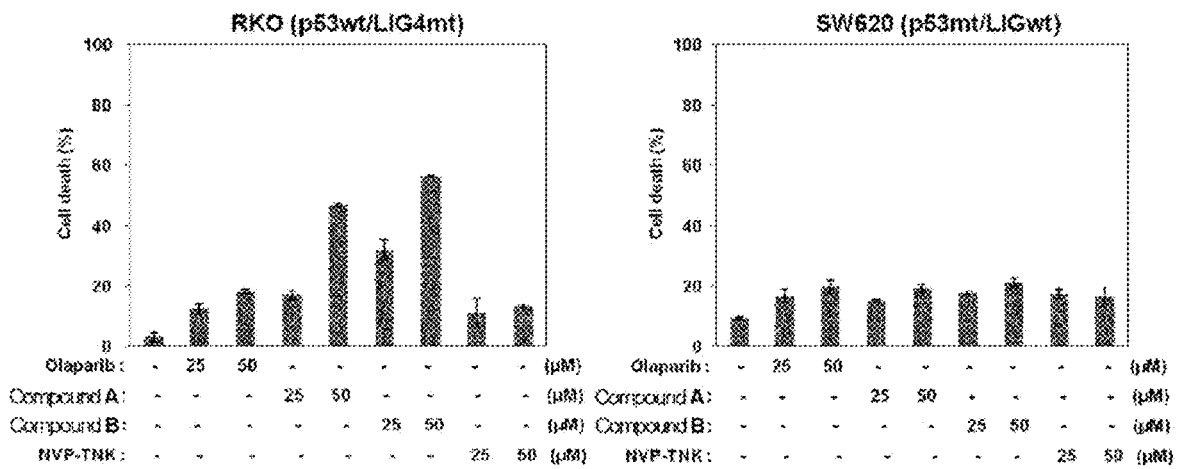
FIGS. 11A to 11D illustrate the results of apoptosis analysis for the treatments of Compound A, Compound B, olaparib and NVP-TNKS656, which are the simultaneous inhibitors against PARP/Tankyrase, in the human colon cancer cell lines RKO (p53 WT/LIG4 MT), SW620 (p53 MT/LIG4 WT), HCT8 (p53 WT/LIG4 WT), and KM12C (p53 MT/LIG4 MT).
Figures 11C, 11D:
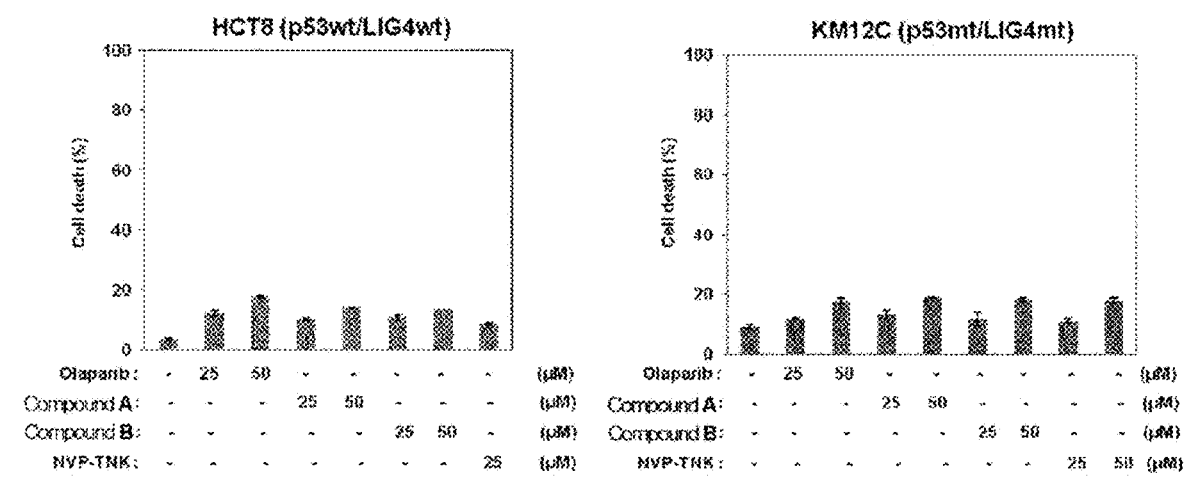

As a result of analyzing the degree of apoptosis by trypan blue straining exclusion assay by treating Compounds A and B, which are novel PARP/Tankyrase simultaneous inhibitors, olaparib, which is a competitive drug PARP inhibitor, and NVP-TNKS656, which is a Tankyrase inhibitor in the human colon cancer cell lines RKO, SW620, HCT8 and KM12C with different p53 genotype and LIG4 genotype, it was possible to observe the apoptosis of Compounds A and B, which are novel PARP/Tankyrase simultaneous inhibitors, in the cell line RKO in which the p53 genotype is a normal type and an LIG4 genotype is a mutant type. Also, it was observed that there was no change in apoptosis by olaparib, which is a competitive drug PARP inhibitor, and NVP-TNKS656, which is a Tankyrase inhibitor (FIG. 11A). No apoptosis occurred by Compounds A and B, olaparib, which is a PARP inhibitor, and NVP-TNKS656, which is a Tankyrase inhibitor in the cell line SW620 in which p53 is a mutant type and LIG4 is a normal type, the cell line HCT8 in which p53 and LIG4 genotypes are normal types, and the cell line KM12C in which p53 and LIG4 genotypes are mutant types, indicating that the apoptosis was shown by Compounds A and B only in case where p53 is a normal type and LIG4 is a mutant type (FIGS. 11A to 11D).

Example 16: Analysis of the Apoptosis of Compound B According to p53 Mutant Type and LIG4 Normal Type Overexpression in the Cell Line RKO in which the p53 Genotype is a Normal Type and an LIG4 Genotype is a Mutant Type As in Example 12, in order to analyze the degree of apoptosis of Compound B, which is a novel PARP/Tankyrase simultaneous inhibitor, according to the expression of a mutant type p53 and a normal type LIG4 when the p53 genotype is a normal type and an LIG4 genotype is a mutant type, the present inventors treated a novel PARP/Tankyrase simultaneous inhibitor, Compound B, and the competitive drug PARP inhibitor, olaparib, while overexpressing the p53 mutant type and the LIG4 normal type in the RKO human colon cancer cell line in which the p53 gene is a normal type and an LIG4 genotype is a mutant type. Then, the number of cells was measured by trypan blue staining assay to confirm the degree of apoptosis. The conditions and methods of the above experiment were as follows: RKO human colon cancer cell line in which the p53 gene is a normal type and an LIG4 gene is a mutant type was cultured under the same condition as in Example 12. p53 mutant type plasmid DNA and plasmid DNA in which an LIG4 genotype is a normal type were infused into cells by means of Lipofectamin 2000 (Invitrogen), and then overexpressed at 37° C. for 48 hours. Then, Compound B, which is a novel PARP/Tankyrase simultaneous inhibitor, and olaparib, which is a competitive drug PARP inhibitor, were treated with each of 25 μM and 50 μM. After 48 hours of culturing, the number of cells was measured by trypan blue staining assay and the degree of apoptosis was confirmed.

Experiment Result

Figure 12A:
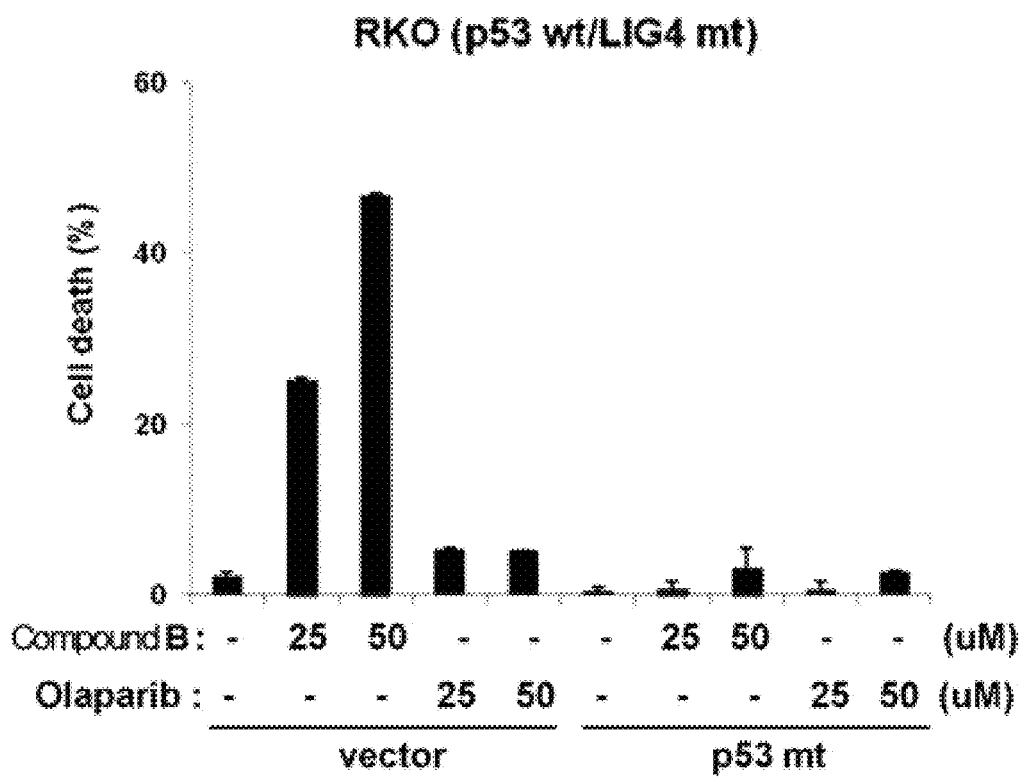
FIGS. 12A and 12B illustrate the results of apoptosis analysis for the treatment of Compound B and olaparib, which are the simultaneous inhibitors against PARP/Tankyrase, overexpressing each of the mutant type p53 and normal type LIG4 in the human colon cancer cell line RKO (p53 WT/LIG4 MT).
Figure 12B:
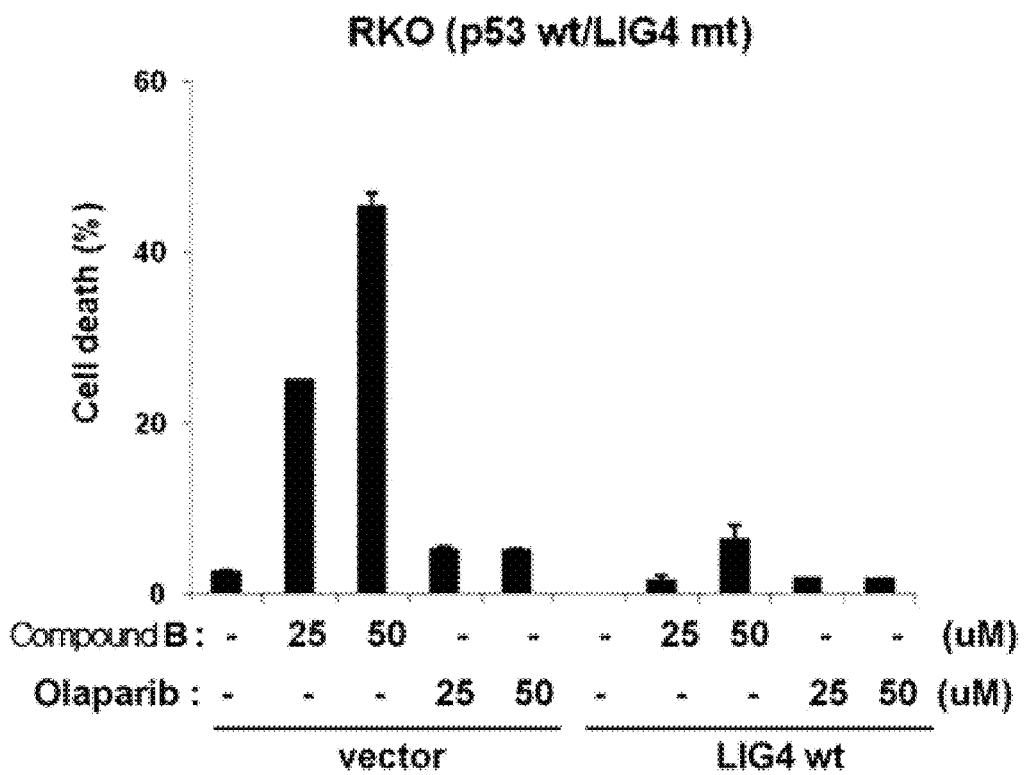

As a result of observing the degree of apoptosis by trypan blue straining exclusion assay by treating Compound B, which is a novel PARP/Tankyrase simultaneous inhibitor, and olaparib, which is a competitive drug PARP inhibitor, while overexpressing the p53 mutant type gene in the human colon cancer cell line RKO in which the p53 genotype is a normal type and an LIG4 genotype is a mutant type, in case where the p53 mutant type gene was overexpressed as compared to a control group (empty) into which the p53 mutant type gene is not inserted, it was observed that the apoptosis was reduced by Compound A, which is a novel PARP/Tankyrase simultaneous inhibitor (FIG. 12A). As a result of observing the degree of apoptosis by trypan blue straining exclusion assay by treating Compound B, which is a novel PARP/Tankyrase simultaneous inhibitor, and olaparib, which is a competitive drug PARP inhibitor, while overexpressing an LIG4 normal type gene in the human colon cancer cell line RKO in which the p53 genotype is a normal type and an LIG4 genotype is a mutant type, in case where an LIG4 normal type gene was overexpressed as compared to a control group (empty) into which an LIG4 normal type gene is not inserted, it was observed that the apoptosis was reduced by Compound B, which is a novel PARP/Tankyrase simultaneous inhibitor. When the p53 is a normal type and an LIG4 is a mutant type, the apoptosis of Compound Bis the highest (FIGS. 12A and 12B).

Example 17: Analysis of the Apoptosis of Compound B According to p53 Mutant Type and LIG4 Normal Type Overexpression in the Cell Line LoVo in which the p53 Genotype is a Normal Type and an LIG4 Genotype is a Mutant Type As in Example 12, in order to analyze the degree of apoptosis of Compound B, which is a novel PARP/Tankyrase simultaneous inhibitor, according to the expression of a mutant type p53 and a normal type LIG4 when the p53 genotype is a normal type and an LIG4 genotype is a mutant type, the present inventors treated a novel PARP/Tankyrase simultaneous inhibitor, Compound B, and the competitive drug PARP inhibitor, olaparib, while overexpressing the p53 mutant type and the LIG4 normal type in the LoVo human colon cancer cell line in which the p53 gene is a normal type and an LIG4 genotype is a mutant type. Then, the number of cells was measured by trypan blue staining assay to confirm the degree of apoptosis. The conditions and methods of the above experiment were the same as the methods of RKO cell culturing and transfection methods of Example 12. Compound B, which is a novel PARP/Tankyrase simultaneous inhibitor, and olaparib, which is a competitive drug PARP inhibitor, were treated with each of 25 μM and 50 μM. After 48 hours of culturing, the number of cells was measured by trypan blue staining assay and the degree of apoptosis was confirmed.

Experiment Result

Figure 13A:
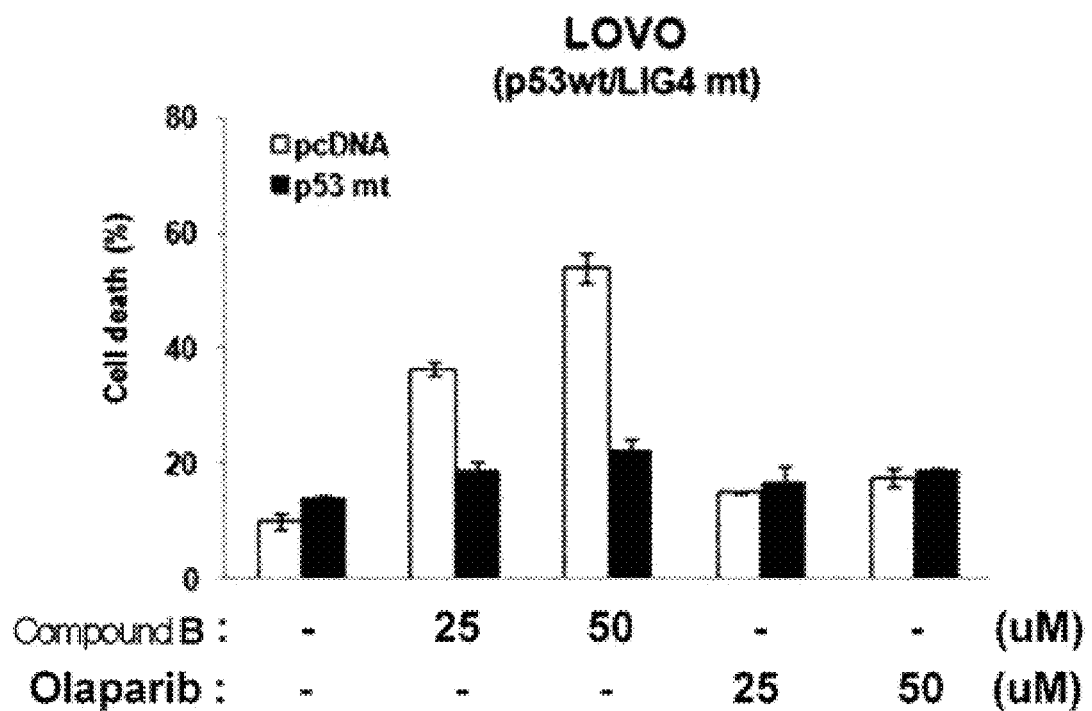
FIGS. 13A and 13B illustrate the results of apoptosis analysis for the treatment of Compound B and olaparib, which are the simultaneous inhibitors against PARP/Tankyrase, overexpressing each of the mutant type p53 and the normal type LIG4 in the human colon cancer cell line LoVo (p53 WT/LIG4 MT).
Figure 13B:
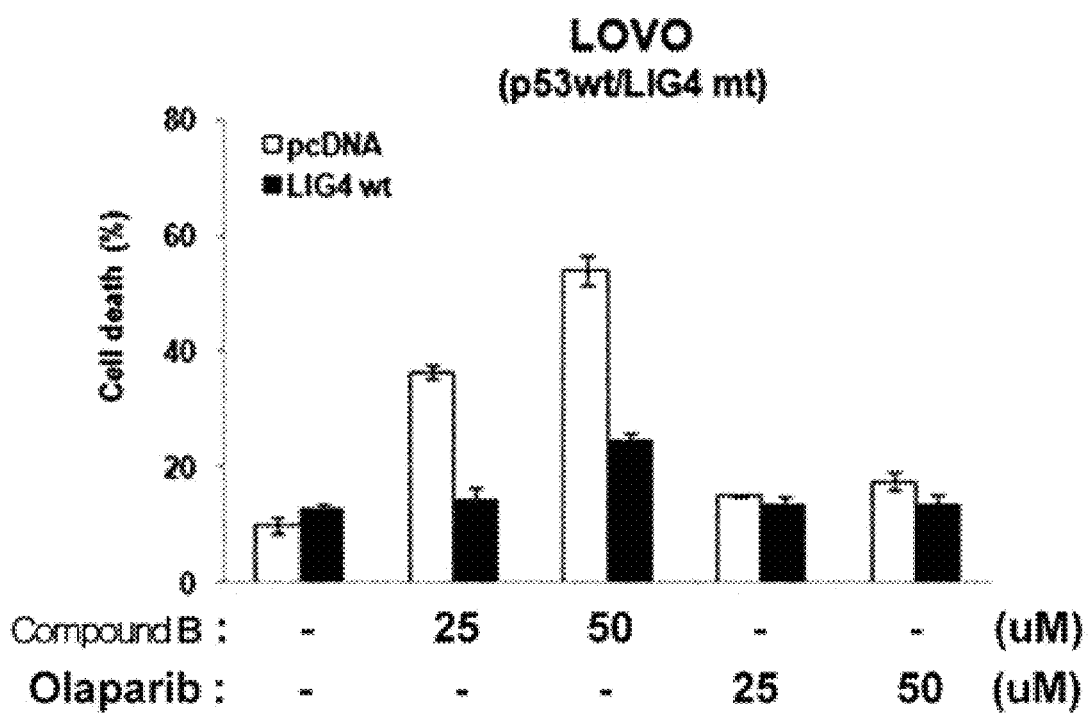

As a result of observing the degree of apoptosis by trypan blue straining exclusion assay by treating Compound B, which is a novel PARP/Tankyrase simultaneous inhibitor, and olaparib, which is a competitive drug PARP inhibitor, while overexpressing the p53 mutant type gene in the human colon cancer cell line LoVo in which the p53 genotype is a normal type and an LIG4 genotype is a mutant type, in case where the p53 mutant type gene was overexpressed as compared to a control group (empty) into which the p53 mutant type gene is not inserted, it was observed that the apoptosis was reduced by Compound B, which is a novel PARP/Tankyrase simultaneous inhibitor (FIG. 13A). As a result of observing the degree of apoptosis by trypan blue straining exclusion assay by treating Compound B, which is a novel PARP/Tankyrase simultaneous inhibitor, and olaparib, which is a competitive drug PARP inhibitor, while overexpressing an LIG4 normal type gene in the human colon cancer cell line LoVo in which the p53 genotype is a normal type and an LIG4 genotype is a mutant type, in case where an LIG4 normal type gene was overexpressed as compared to a control group (empty) into which an LIG4 normal type gene is not inserted, it was observed that the apoptosis was reduced by Compound B, which is a novel PARP/Tankyrase simultaneous inhibitor (FIG. 13B). When the p53 is a normal type and an LIG4 is a mutant type, the apoptosis of Compound B is the highest (FIGS. 13A and 13B).

Example 18: DNA Damage and Apoptosis Analysis of Compound B According to p53 Mutant Type and LIG4 Normal Type Overexpression in the Cell Line LoVo in which the p53 Genotype is a Normal Type and an LIG4 Genotype is a Mutant Type In order to analyze the degree of DNA damage and the degree of apoptosis of Compound B, which is a novel PARP/Tankyrase simultaneous inhibitor, according to the expression of a mutant type p53 and a normal type LIG4 when the p53 genotype is a normal type and an LIG4 genotype is a mutant type, the present inventors cultured and treated the LoVo human colon cancer cell line in which the p53 genotype is a normal type and an LIG4 genotype is a mutant type under the same condition as in Example 17. DNA damage was confirmed by the Western blot method at the expression level of r-H2AX, and the degree of apoptosis was confirmed by the same method as Example 11 at the expression level of cleaved caspase 3.

Experiment Result

Figure 14A:
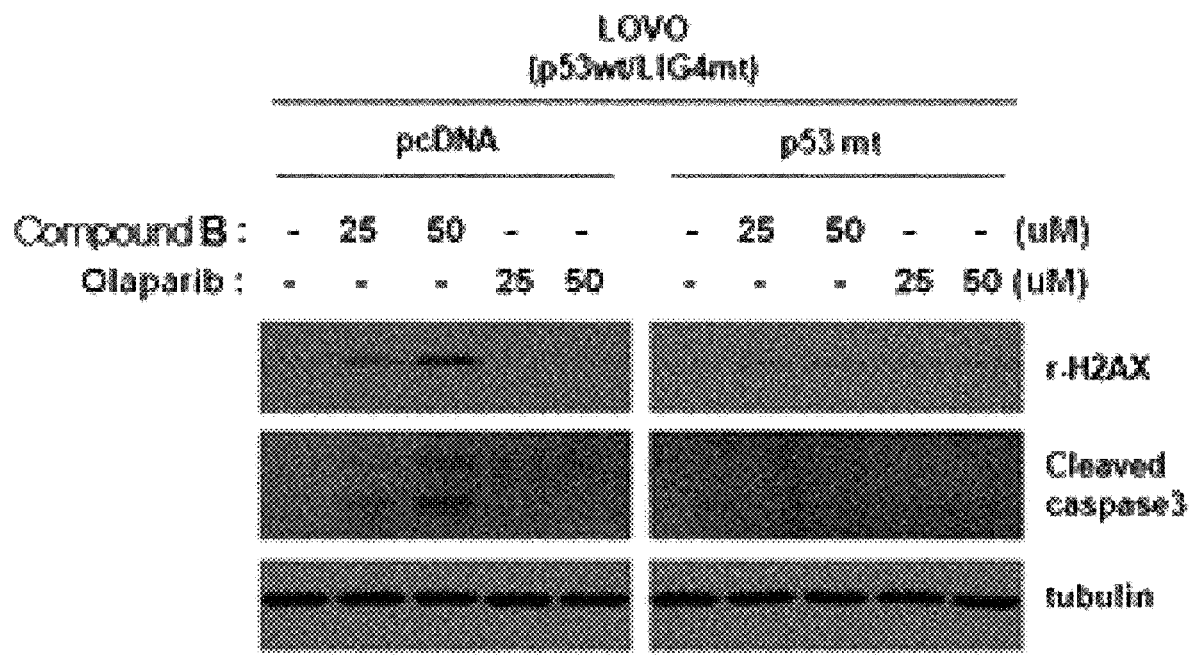
FIGS. 14A and 14B illustrate DNA damage and apoptosis for the treatment of Compound B and olaparib, which are simultaneous inhibitors against PARP/Tankyrase, overexpressing each of the mutant type p53 and the normal type LIG4 in the human colon cancer cell line LoVo (p53 WT/LIG4 MT) through Western blot.
Figure 14B:
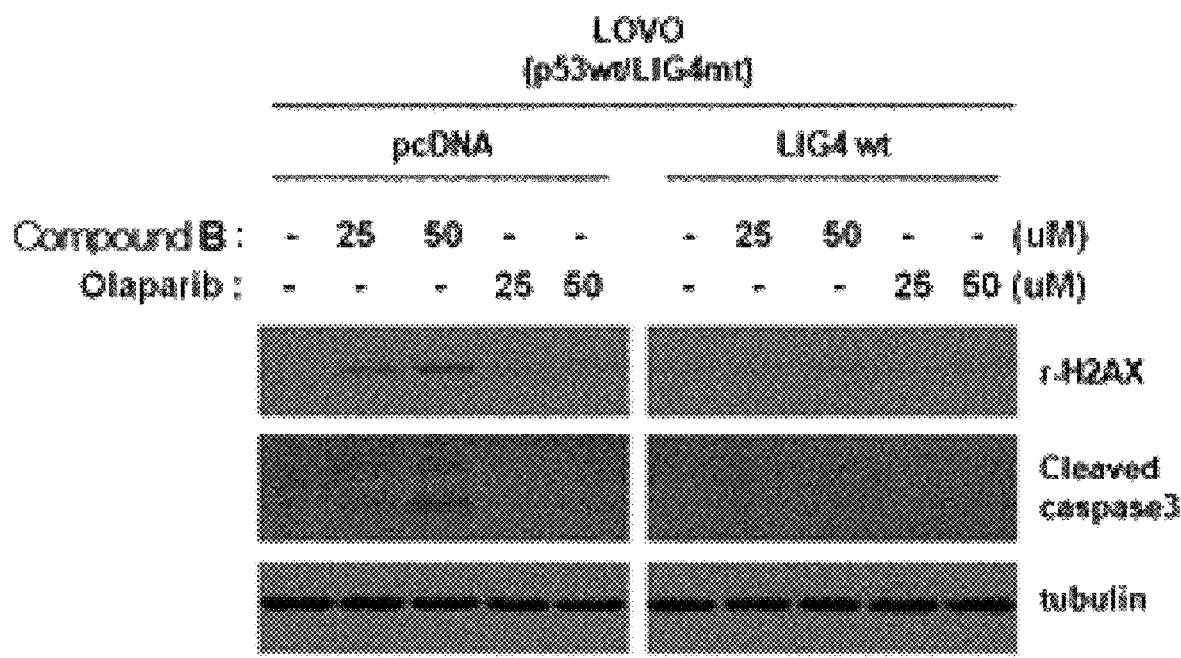

As a result of observing the degree of DNA damage and the degree of apoptosis by western blot by means of the expression amount of r-H2AX and cleaved caspase 3 by treating Compound B, which is a novel PARP/Tankyrase simultaneous inhibitor, and olaparib, which is a competitive drug PARP inhibitor, while overexpressing the p53 mutant type gene in the human colon cancer cell line LoVo in which the p53 genotype is a normal type and an LIG4 genotype is a mutant type, in case where the p53 mutant type gene was overexpressed as compared to a control group (empty) into which the p53 mutant type gene is not inserted, it was observed that the expression of r-H2AX and the expression amount of cleaved caspase 3 were reduced by Compound B, which is a novel PARP/Tankyrase simultaneous inhibitor (FIG. 14A). As a result of observing the degree of DNA damage and the degree of apoptosis by western blot by means of the expression amount of r-H2AX and cleaved caspase 3 by treating Compound B, which is a novel PARP/Tankyrase simultaneous inhibitor, and olaparib, which is a competitive drug PARP inhibitor, while overexpressing the p53 mutant type gene in the human colon cancer cell line LoVo in which a p53 genotype is a normal type and an LIG4 genotype is a mutant type, in case where an LIG4 normal type gene was overexpressed as compared to a control group (empty) into which an LIG4 normal type gene is not inserted, it was observed that the expression of r-H2AX and the expression amount of cleaved caspase 3 were reduced by Compound B, which is a novel PARP/Tankyrase simultaneous inhibitor (FIG. 14B). Only when a p53 is a normal type and an LIG4 is a mutant type, the DNA damage and apoptosis of Compound B were induced (FIG. 14).

Example 19: Tumor Inhibition Effect on Compound A and Olaparib in a Xenotransplantation Animal Model Using a Cell Line RKO in which the p53 Genotype is a Normal Type and an LIG4 Genotype is a Mutant Type In order to analyze the tumor inhibition effect on an in vivo animal model for Compound A, which is a novel PARP/Tankyrase simultaneous inhibitor, and an in vivo animal model for olaparib, when the p53 genotype is a normal type and an LIG4 genotype is a mutant type, the present inventors transplanted the RKO human colon cancer cell line in which a p53 genotype is a normal type and an LIG4 genotype is a mutant type into a 6-week-old nude mouse (BALB/c-nude, purchased from the central experimental animal) and administered with Compound A, which is a novel PARP/Tankyrase simultaneous inhibitor, and olaparib, which is a competitive drug PARP inhibitor. Then, the size of tumor was measured to confirm the degree of tumor inhibition effect. The conditions and methods of the experiment were as follows: RKO human colon cancer cell line in which a p53 gene is a normal type and an LIG4 gene is a mutant type was cultured in RPMI1640 (10% FBS, 1% penicillin/streptomycin). When the size of the tumor reached 100 mm$^3$ after being transplanted into a nude mouse per 1×10$^7$, Compound A, which is a novel PARP/Tankyrase simultaneous inhibitor, and olaparib, which is a competitive drug PARP inhibitor, were orally administered at 25 mpk and 50 mpk daily for a total of 27 days. The size of a tumor was measured every three days. After the completion of drug administration, the tumors were harvested and weighed.

Experiment Result

Figure 15A:
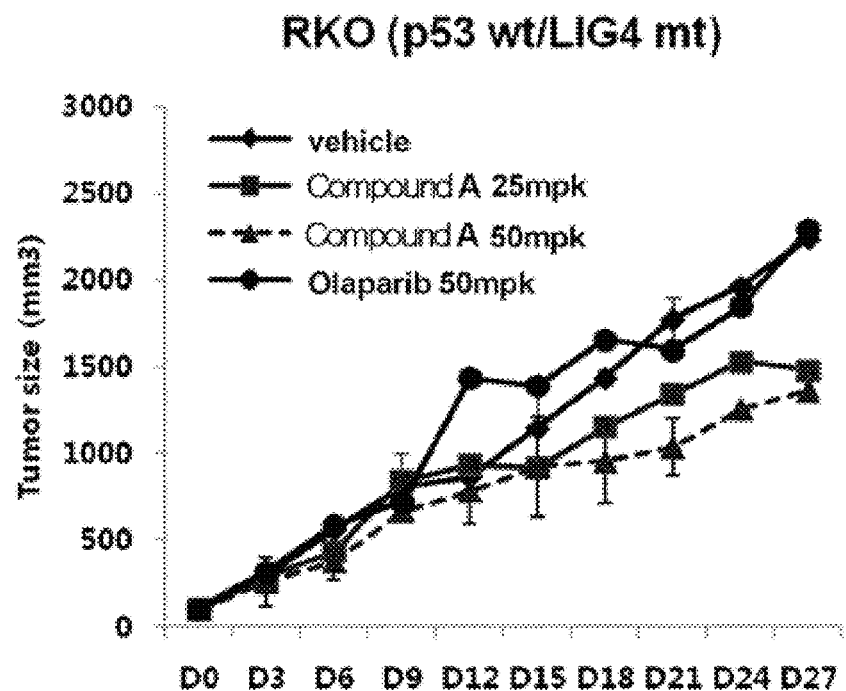
FIGS. 15A and 15B illustrate the results of tumor inhibition analysis of Compound A and olaparib, which are simultaneous inhibitors against PARP/Tankyrase, in an in vivo model of xenograft model using the human colon cancer cell line RKO (p53 WT/LIG4 MT).
Figure 15B:
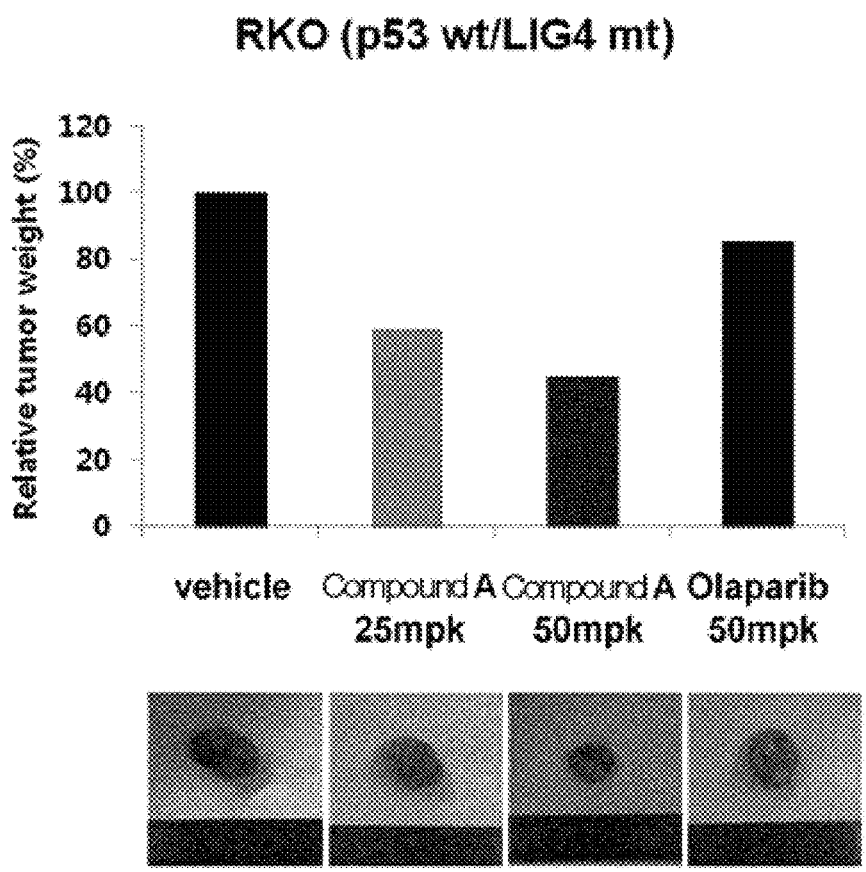

As a result of observing the degree of a tumor inhibition effect by administrating Compound A, which is a novel PARP/Tankyrase simultaneous inhibitor, and olaparib, which is a competitive drug PARP inhibitor in the human colon cancer cell line RKO in which a p53 genotype is a normal type and an LIG4 genotype is a mutant type, the tumor inhibition effect of Compound A, which is a novel PARP/Tankyrase simultaneous inhibitor, the size of the tumor was reduced compared with the group administered with olaparib, which is a competitive drug PARP inhibitor, and the weight of a tumor was reduced, indicating that the tumor inhibition effect for Compound A was produced in case where p53 is a normal type and LIG4 is a mutant type (FIGS. 15A and 15B).

Example 20: Tumor Inhibition Effect Analysis on Compound A and Olaparib in a Xenotransplantation Animal Model Using a Cell Line SW620 in which the p53 Genotype is a Mutant Type and an LIG4 Genotype is a Normal Type In order to analyze the tumor inhibition effect on Compound A, which is a novel PARP/Tankyrase simultaneous inhibitor, in an in vivo animal model when the p53 genotype is a mutant type and an LIG4 genotype is a normal type, the present inventors transplanted the SW620 human colon cancer cell line in which a p53 genotype is a mutant type and an LIG4 genotype is a normal type into a 6-week-old nude mouse (BALB/c-nude, purchased from the central experimental animal) and administered with Compound A, which is a novel PARP/Tankyrase simultaneous inhibitor, and olaparib, which is a competitive drug PARP inhibitor. Then, the size of tumor was measured to confirm the degree of tumor inhibition effect. The conditions and methods of the experiment were as follows: SW620 human colon cancer cell line in which a p53 gene is a mutant type and an LIG4 gene is a normal type was cultured in RPMI1640 (10% FBS, 1% penicillin/streptomycin). When the size of the tumor reached 100 mm$^3$ after being transplanted into a nude mouse per 1×10$^7$, Compound A, which is a novel PARP/Tankyrase simultaneous inhibitor, and olaparib, which is a competitive drug PARP inhibitor, were orally administered at 25 mpk and 50 mpk daily for a total of 27 days. The size of a tumor was measured every three days. After the completion of drug administration, the tumors were harvested and weighed.

Experiment Result

Figure 16A:
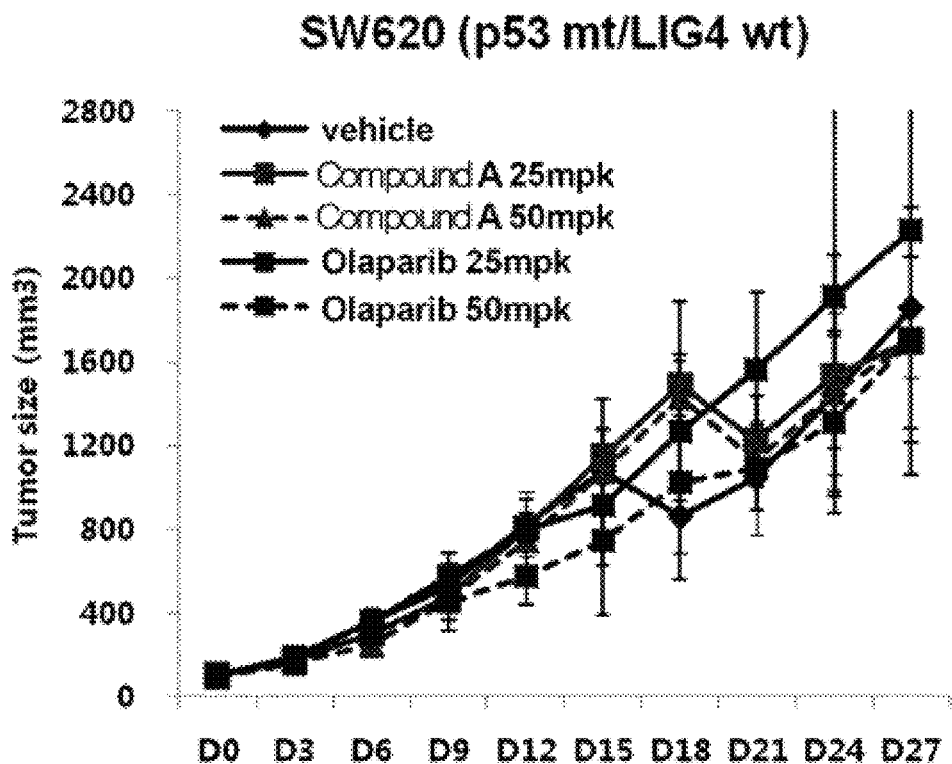
FIGS. 16A and 16B illustrate the results of tumor inhibition analysis for the administration of Compound A and olaparib, which are simultaneous inhibitors against PARP/Tankyrase, in an in vivo model of xenograft model using the human colon cancer cell line SW620 (p53 MT/LIG4 WT).
Figure 16B:
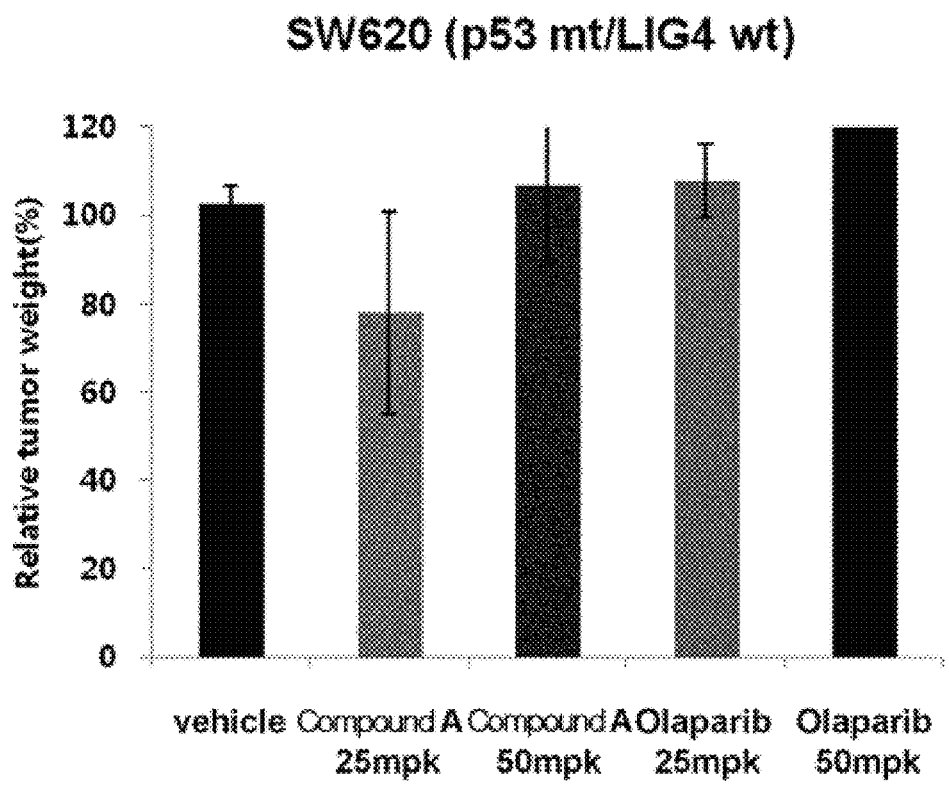

As a result of observing the degree of a tumor inhibition effect by administrating Compound A, which is a novel PARP/Tankyrase simultaneous inhibitor, and olaparib, which is a competitive drug PARP inhibitor in the human colon cancer cell line SW620 in which a p53 genotype is a mutant type and an LIG4 genotype is a normal type, there was no change both in tumor size and weight by Compound A, which is a novel PARP/Tankyrase simultaneous inhibitor, and olaparib, which is a competitive drug PARP inhibitor, indicating that no tumor inhibition effect for Compound A and olaparib was produced in case where p53 is a normal type and LIG4 is a mutant type (FIGS. 16A and 16B).

Example 21: Analysis of Tumor Inhibition Effect on Compound A in a Xenotransplantation Animal Model Using a Cell Line KM12C in which a p53 Genotype and an LIG4 Genotype are Mutant Types In order to analyze the tumor inhibition effect on Compound A, which is a novel PARP/Tankyrase simultaneous inhibitor, in an in vivo animal model when a p53 genotype and an LIG4 genotype are mutant types, the present inventors transplanted the KM12C human colon cancer cell line in which a p53 genotype and an LIG4 genotype are mutant types into a 6-week-old nude mouse (BALB/c-nude, purchased from the central experimental animal) and administered with Compound A, which is a novel PARP/Tankyrase simultaneous inhibitor, and olaparib, which is a competitive drug PARP inhibitor. Then, the size of tumor was measured to confirm the degree of tumor inhibition effect. The conditions and methods of the experiment were as follows: KM12C human colon cancer cell line in which a p53 genotype and an LIG4 genotype are mutant types was cultured in RPMI1640 (10% FBS, 1% penicillin/streptomycin). When the size of the tumor reached 100 mm$^3$ after being transplanted into a nude mouse per 1×10$^7$, Compound A, which is a novel PARP/Tankyrase simultaneous inhibitor, and olaparib, which is a competitive drug PARP inhibitor, were orally administered at 25 mpk and 50 mpk daily for a total of 18 days. The size of a tumor was measured every three days. After the completion of drug administration, the tumors were harvested and weighed.

Experiment Result

Figure 17A:
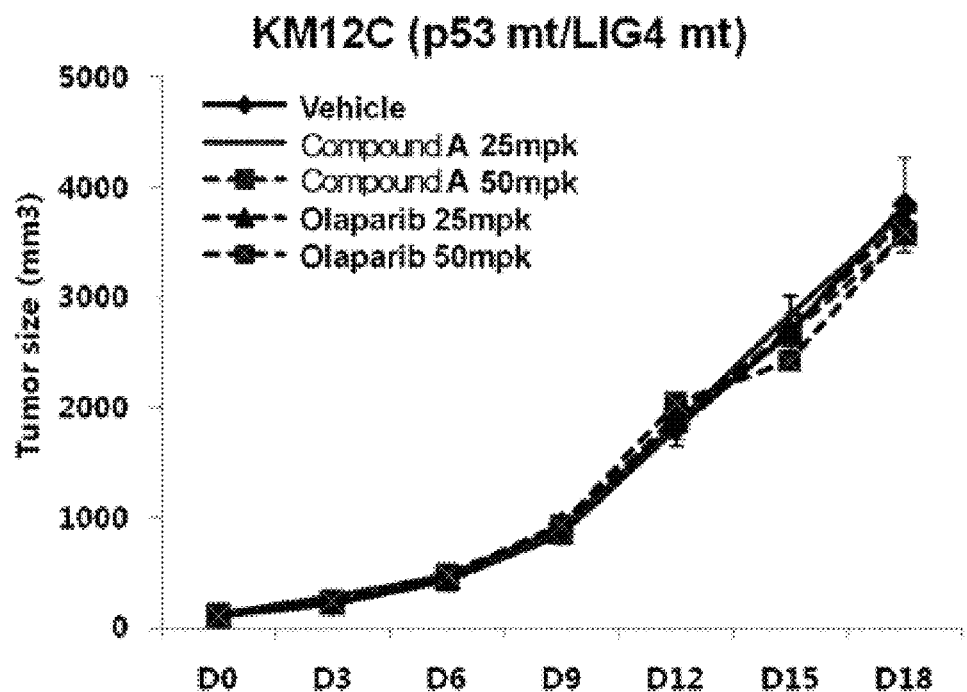
FIGS. 17A and 17B illustrate the results of tumor inhibition analysis for the administration of Compound A and olaparib, which are simultaneous inhibitors against PARP/Tankyrase, in an in vivo model of xenograft model using the human colon cancer cell line KM12C (p53 MT/LIG4 MT)
Figure 17B:
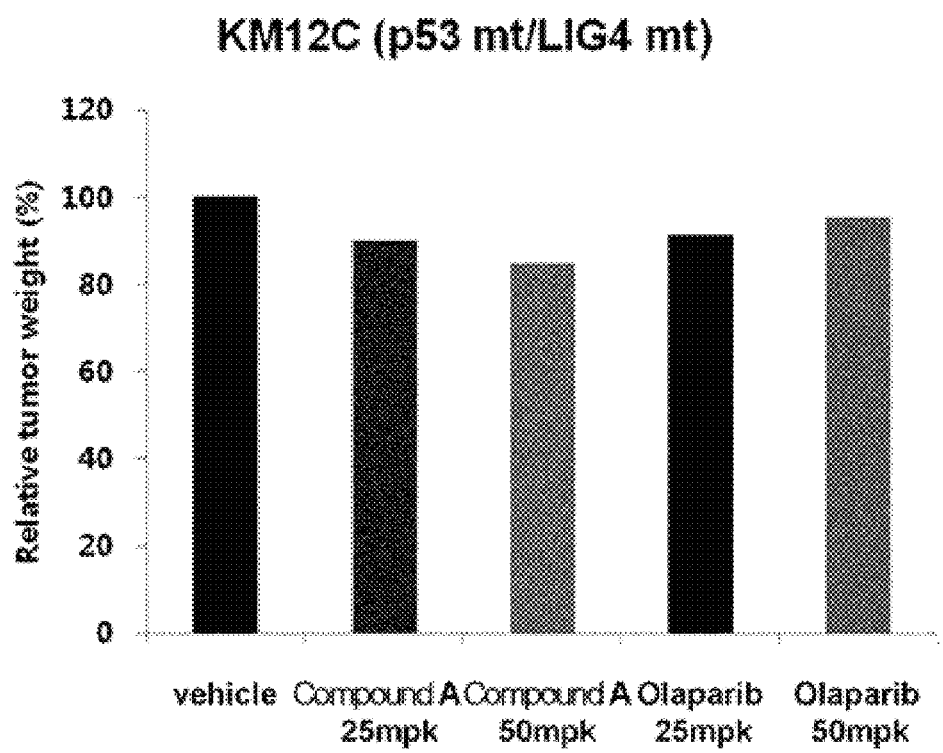

As a result of observing the degree of a tumor inhibition effect by administrating Compound A, which is a novel PARP/Tankyrase simultaneous inhibitor, and olaparib, which is a competitive drug PARP inhibitor in the human colon cancer cell line KM12C in which a p53 genotype and an LIG4 genotype are mutant types, there was no change both in tumor size and weight by Compound A, which is a novel PARP/Tankyrase simultaneous inhibitor, and olaparib, which is a competitive drug PARP inhibitor, indicating that no tumor inhibition effect for Compound A and olaparib was produced in case where both p53 and LIG4 are mutant types (FIGS. 17A and 17B).

Example 22: Analysis of Tumor Inhibition Effect on Compound B and Olaparib in a Xenotransplantation Animal Model Using a Cell Line RKO in which the p53 Genotype is a Normal Type and an LIG4 Genotype is a Mutant Type In order to analyze the tumor inhibition effect on an in vivo animal model for Compound B, which is a novel PARP/Tankyrase simultaneous inhibitor, and olaparib, when the p53 genotype is a normal type and an LIG4 genotype is a mutant type, the present inventors transplanted the RKO human colon cancer cell line in which a p53 genotype is a normal type and an LIG4 genotype is a mutant type into a 6-week-old nude mouse (BALB/c-nude, purchased from the central experimental animal) and administered with Compound B, which is a novel PARP/Tankyrase simultaneous inhibitor, and olaparib, which is a competitive drug PARP inhibitor. Then, the size of tumor was measured to confirm the degree of tumor inhibition effect. The conditions and methods of the experiment were as follows: RKO human colon cancer cell line in which a p53 gene is a normal type and an LIG4 gene is a mutant type was cultured in RPMI1640 (10% FBS, 1% penicillin/streptomycin). When the size of the tumor reached 100 mm$^3$ after being transplanted into a nude mouse per 1×10$^7$, Compound B, which is a novel PARP/Tankyrase simultaneous inhibitor, and olaparib, which is a competitive drug PARP inhibitor, were orally administered at 25 mpk and 50 mpk daily for a total of 27 days. The size of a tumor was measured every three days. After the completion of drug administration, the tumors were harvested and weighed.

Experiment Result

Figure 18A:
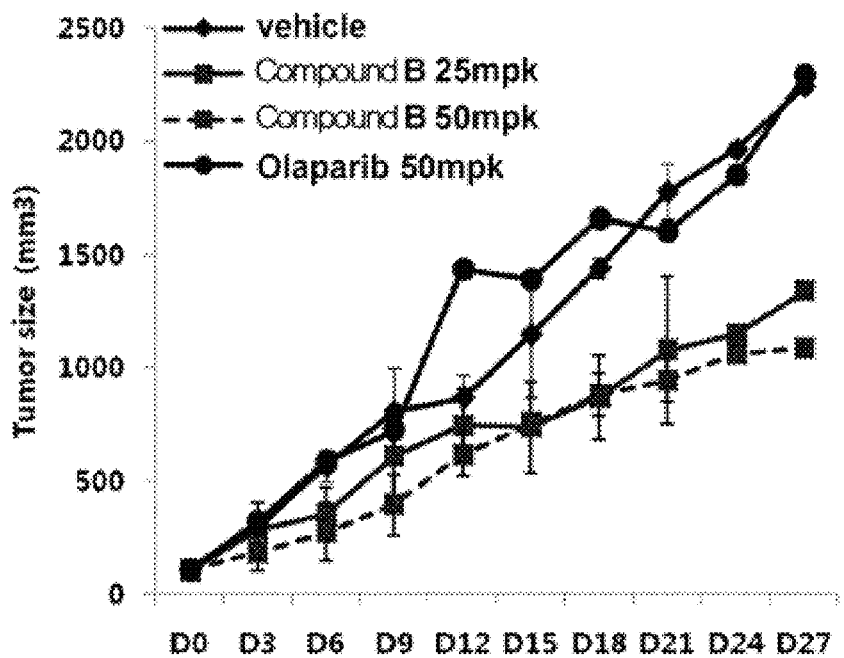
FIGS. 18A and 18B illustrate the results of tumor inhibition analysis for the administration of Compound B and olaparib, which are simultaneous inhibitors against PARP/Tankyrase, in an in vivo model of xenograft model using the human colon cancer cell line RKO (p53 WT/LIG4 MT).
Figure 18B:
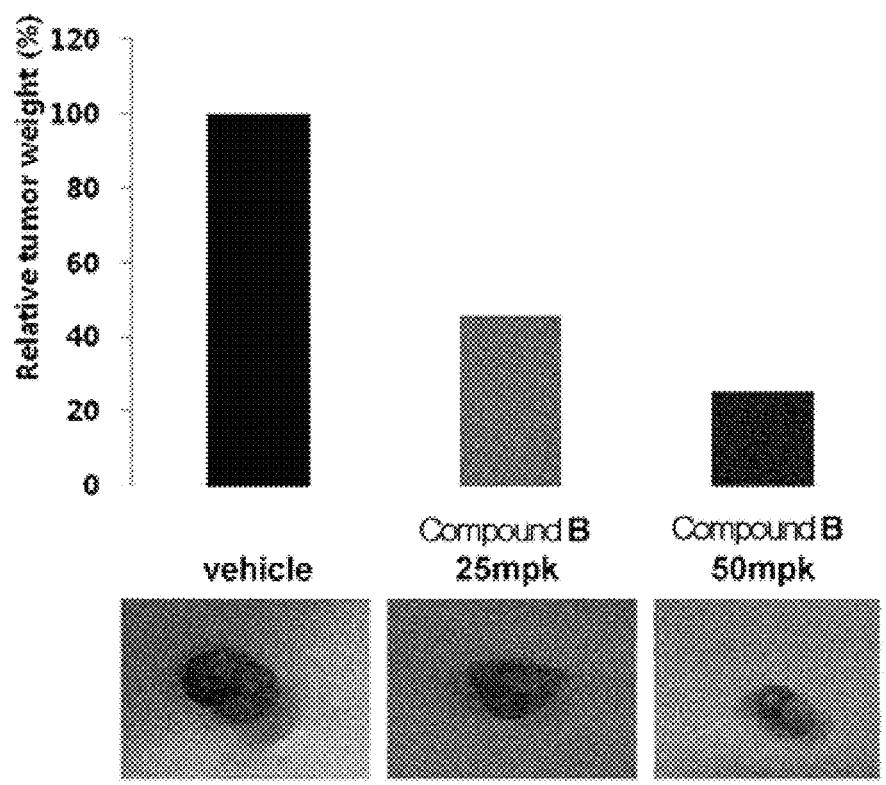

As a result of observing the degree of a tumor inhibition effect by administrating Compound B, which is a novel PARP/Tankyrase simultaneous inhibitor, and olaparib, which is a competitive drug PARP inhibitor in the human colon cancer cell line RKO in which a p53 genotype is a normal type and an LIG4 genotype is a mutant type, the tumor inhibition effect of Compound B, which is a novel PARP/Tankyrase simultaneous inhibitor, the size of the tumor was reduced compared with the group administered with olaparib, which is a competitive drug PARP inhibitor, and the weight of a tumor was reduced, indicating that the tumor inhibition effect for Compound B was produced in case where p53 is a normal type and LIG4 is a mutant type (FIGS. 18A and 18B).

Example 23: Analysis of Tumor Inhibition Effect on Compound B in a Xenotransplantation Animal Model Using a Cell Line KM12C in which a p53 Genotype and an LIG4 Genotype are Mutant Types In order to analyze the tumor inhibition effect on Compound B, which is a novel PARP/Tankyrase simultaneous inhibitor, in an in vivo animal model when a p53 genotype and an LIG4 genotype are mutant types, the present inventors transplanted the KM12C human colon cancer cell line in which a p53 genotype and an LIG4 genotype are mutant types into a 6-week-old nude mouse (BALB/c-nude, purchased from the central experimental animal) and administered with Compound B, which is a novel PARP/Tankyrase simultaneous inhibitor. Then, the size of tumor was measured to confirm the degree of tumor inhibition effect. The conditions and methods of the experiment were as follows: KM12C human colon cancer cell line in which a p53 genotype and an LIG4 genotype are mutant types was cultured in RPMI1640 (10% FBS, 1% penicillin/streptomycin). When the size of the tumor reached 100 mm$^3$ after being transplanted into a nude mouse per 1×10$^7$, Compound B, which is a novel PARP/Tankyrase simultaneous inhibitor, was orally administered at 25 mpk and 50 mpk daily for a total of 15 days. The size of a tumor was measured every three days. After the completion of drug administration, the tumors were harvested and weighed.

Experiment Result

Figure 19A:
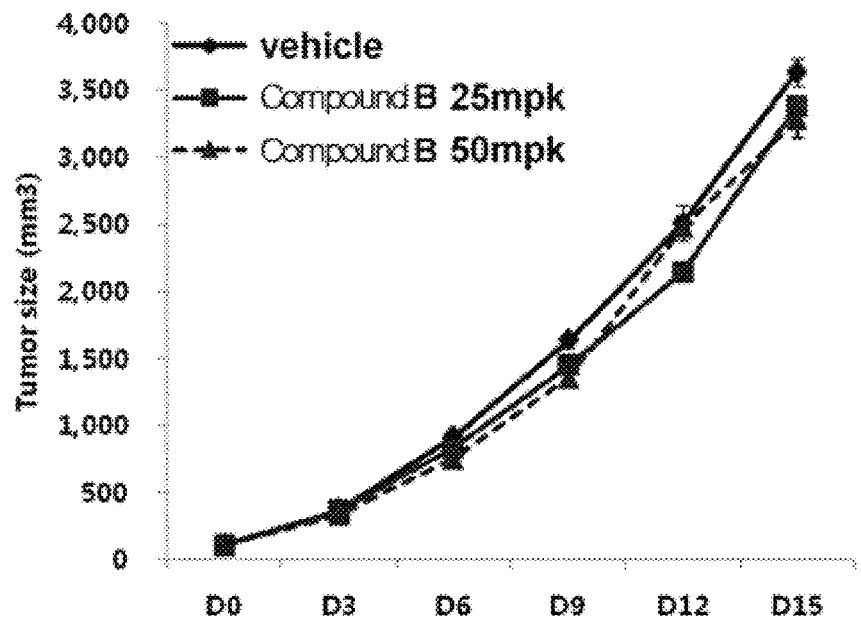
FIGS. 19A and 19B illustrate the results of tumor inhibition analysis for the administration of Compound B, which is a simultaneous inhibitor against PARP/Tankyrase, in an in vivo model of xenograft model using the human colon cancer cell line KM12C (p53 MT/LIG4 MT).
Figure 19B:
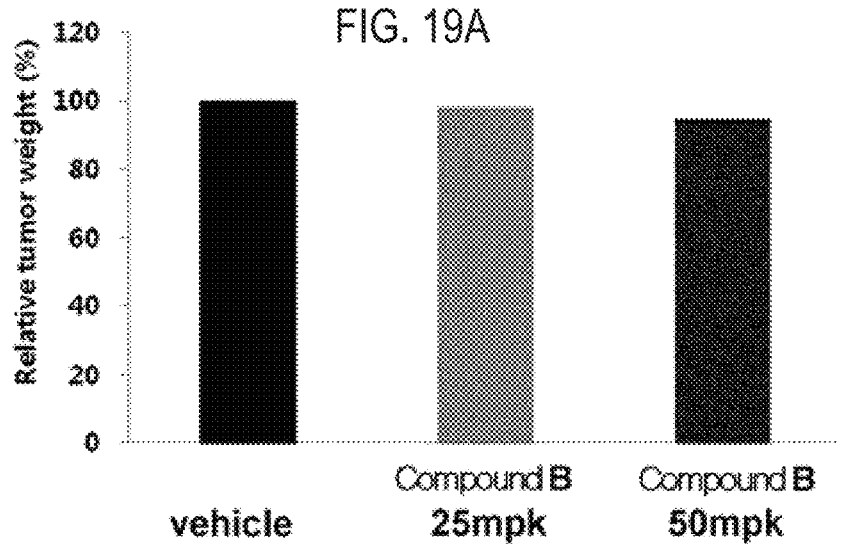
Figure 19B:
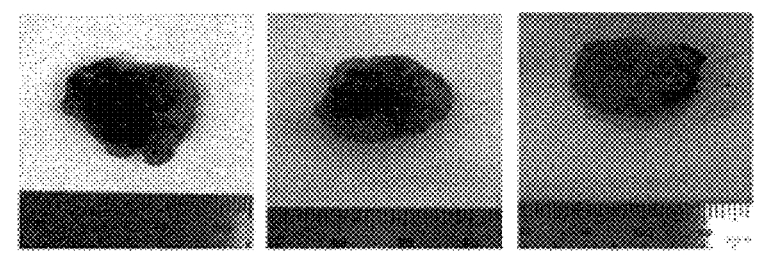

As a result of observing the degree of a tumor inhibition effect by administrating Compound B, which is a novel PARP/Tankyrase simultaneous inhibitor, in the human colon cancer cell line KM12C in which in which a p53 genotype and an LIG4 genotype are mutant types, there was no change both in tumor size and weight by Compound B, which is a novel PARP/Tankyrase simultaneous inhibitor, indicating that no tumor inhibition effect for Compound B was produced in case where both p53 and LIG4 are mutant types (FIGS. 19A and 19B).

Example 24: Analysis of LIG4 Genotype in Colon Cancer Patient-Derived Cells

In order to confirm an LIG4 genotype in the colon cancer patient-derived cells, the present inventors analyzed the mutation/deficiency of an LIG4 genotype in 36 colon cancer patient-derived cell lines through RT-PCR and sequencing. The conditions and methods of the experiment were as follows: A total of 36 colon cancer patient-derived cell lines were subjected to total RNA extraction with Trizol RNA extraction method using a homogenizer, and 500 ng of total RNA was re-synthesized into cDNA and PCR was performed using LIG4 primer (SEQ ID NO: 12; LIG4 primer Exon1-1 forward primer 5'-TTGCTTTACTAGTTAAAC-GAGAAGATTCA-3', SEQ ID NO: 13; LIG4 primer Exon1-1 reverse primer 5'-TTCGTTCTAAAGTTGAACA-CAAATCTG-3', SEQ ID NO: 8; LIG4 primer Exon2-1 forward primer 5'-GCTAGCTGCTATTGCAGATATT-GAGC-3', SEQ ID NO: 9; LIG4 primer Exon2-1 reverse primer 5'-AGAACCTTCAGTAGGAGAAGCACCAA-3', SEQ ID. NO.: 10; LIG4 primer Exon2-2 forward primer 5'-CCTGGTGAGAAGCCATCTGT-3', SEQ ID. NO.: 11; LIG4 primer Exon2-2 reverse primer 5'-GCCTTC-CCCCTAAGTTGTTC-3'). After electrophoresis on 1% agarose gel; the mutant analysis was confirmed by Sanger sequencing of the PCR product in which the expression of LIG4 was confirmed through Et-Br staining.

Experiment Result

As a result of analyzing whether there is any mutation in the C8, C27, G833, and T1704 sites of LIG4 in 36 colon cancer patient-derived cell lines, mutations in LIG4 were analyzed in 14 colon cancer patient-derived cell lines (Table 5).

TABLE 5

| Human colorectal primary cancer cell | | | | |
|---|---|---|---|---|
| | LIG4 (DNA ligase IV) mutation | | | |
| No. | C8T | C26T | G833A | T1704C |
| 1 | WT | WT | WT | WT |
| 2 | WT | MT | WT | WT |
| 3 | WT | MT | WT | WT |
| 4 | WT | MT | WT | WT |
| 5 | WT | WT | WT | WT |
| 6 | WT | MT | WT | WT |
| 7 | WT | MT | WT | WT |
| 8 | WT | WT | WT | WT |
| 9 | WT | WT | WT | WT |
| 10 | WT | WT | WT | WT |
| 11 | WT | WT | WT | WT |
| 12 | WT | MT | WT | WT |
| 13 | WT | WT | WT | WT |
| 14 | WT | WT | WT | WT |
| 15 | WT | WT | WT | WT |
| 16 | WT | MT | WT | WT |

TABLE 5-continued

Human colorectal primary cancer cell

| | LIG4 (DNA ligase IV) mutation | | | |
|---|---|---|---|---|
| No. | C8T | C26T | G833A | T1704C |
| 17 | WT | WT | WT | WT |
| 18 | WT | WT | WT | WT |
| 19 | WT | WT | WT | WT |
| 20 | WT | WT | WT | WT |
| 21 | WT | WT | WT | WT |
| 22 | WT | WT | WT | WT |
| 23 | WT | MT | WT | WT |
| 24 | WT | MT | WT | WT |
| 25 | WT | WT | WT | WT |
| 26 | WT | WT | WT | WT |
| 27 | WT | WT | WT | WT |
| 28 | WT | WT | WT | WT |
| 29 | WT | MT | WT | WT |
| 30 | WT | MT | WT | WT |
| 31 | MT | WT | WT | WT |
| 32 | WT | WT | WT | WT |
| 33 | WT | MT | WT | WT |
| 34 | WT | WT | WT | WT |
| 35 | WT | MT | WT | WT |
| 36 | WT | WT | WT | WT |

Example 25: Analysis of LIG4 Genotypes in Colon Cancer Patient Tissues

In order to confirm an LIG4 genotype in the colon cancer patient tissues, the present inventors analyzed the mutation/deficiency of an LIG4 genotype in 39 colon cancer patient-derived tissues through RT-PCR and sequencing. The conditions and methods of the experiment were as follows: A total of 39 colon cancer patient-derived tissues were subjected to total RNA extraction with Trizol RNA extraction method using a homogenizer, and 500 ng of total RNA was re-synthesized into cDNA and PCR was performed using LIG4 primer (SEQ ID NO: 12; LIG4 primer Exon1-1 forward primer 5'-TTGCTTTACTAGTTAAACGA-GAAGATTCA-3', SEQ ID NO: 13; LIG4 primer Exon1-1 reverse primer 5'-TTCGTTCTAAAGTTGAACA-CAAATCTG-3', SEQ ID NO: 8; LIG4 primer Exon2-1 forward primer 5'-GCTAGCTGCTATTGCAGATATT-GAGC-3', SEQ ID NO: 9; LIG4 primer Exon2-1 reverse primer 5'-AGAACCTTCAGTAGGAGAAGCACCAA-3', SEQ ID. NO.: 10; LIG4 primer Exon2-2 forward primer 5'-CCTGGTGAGAAGCCATCTGT-3', SEQ ID. NO.: 11; LIG4 primer Exon2-2 reverse primer 5'-GCCTTC-CCCCTAAGTTGTTC-3'). After electrophoresis on 1% agarose gel, the mutant analysis was confirmed by sanger sequencing of the PCR product in which the expression of LIG4 was confirmed through Et-Br staining.

Experiment Result

As a result of analyzing whether there is any mutation in the C8, C27, G833, and T1704 sites of LIG4 in 39 colon cancer patient tissues, mutations in LIG4 were analyzed in 9 colon cancer patient tissues (Table 6).

TABLE 6

Human colorectal cancer tissue

| | LIG4 (DNA ligase IV) mutation | | | |
|---|---|---|---|---|
| No. | C8T | C26T | G833A | T1704C |
| 1 | WT | WT | WT | WT |
| 2 | WT | WT | WT | WT |
| 3 | WT | WT | WT | WT |

TABLE 6-continued

Human colorectal cancer tissue

| | LIG4 (DNA ligase IV) mutation | | | |
|---|---|---|---|---|
| No. | C8T | C26T | G833A | T1704C |
| 4 | WT | MT | WT | WT |
| 5 | WT | WT | WT | WT |
| 6 | WT | WT | WT | WT |
| 7 | WT | MT | WT | WT |
| 8 | WT | WT | WT | WT |
| 9 | WT | WT | WT | WT |
| 10 | WT | WT | WT | WT |
| 11 | WT | WT | WT | WT |
| 12 | WT | MT | WT | WT |
| 13 | WT | WT | WT | WT |
| 14 | WT | WT | WT | WT |
| 15 | WT | WT | WT | WT |
| 16 | WT | WT | WT | WT |
| 17 | WT | WT | WT | WT |
| 18 | WT | WT | WT | WT |
| 19 | WT | WT | WT | WT |
| 20 | WT | WT | WT | WT |
| 21 | WT | WT | WT | WT |
| 22 | WT | WT | WT | WT |
| 23 | WT | WT | WT | WT |
| 24 | WT | WT | WT | WT |
| 25 | WT | WT | WT | WT |
| 26 | WT | WT | WT | WT |
| 27 | WT | WT | WT | WT |
| 28 | WT | WT | WT | WT |
| 29 | WT | WT | WT | WT |
| 30 | WT | WT | WT | WT |
| 31 | WT | WT | WT | WT |
| 32 | WT | WT | WT | WT |
| 33 | WT | WT | WT | WT |
| 34 | WT | WT | WT | WT |
| 35 | WT | WT | WT | WT |
| 36 | WT | WT | WT | WT |
| 37 | WT | WT | WT | WT |
| 38 | WT | WT | WT | WT |
| 39 | WT | WT | WT | WT |

Example 26: Analysis of Drug Efficacy in Colon Cancer Patient-Derived Cells in which a p53 Genotype is a Normal Type and an LIG4 Genotype is a Normal or Mutant Type In order to analyze the degree of drug efficiency of Compound B, which is a novel PARP/Tankyrase simultaneous inhibitor, in the colon cancer patient-derived cells 11-CT-79558D (p53 WT/LIG4 MT), 11-CT-80464B (p53 WT/LIG4 MT) and 11CT-94575 (p53 WT/LIG4 WT), 13CT-78649B (p53 WT/LIG4 WT) in which a p53 genotype is a normal type and an LIG4 genotype is a normal or mutant type, four different types of human colon cancer patient-derived cells REBM (Renal Growth Basal Medium; 5% FBS, 1% penicillin/streptomycin) in which a p53 genotype is a normal type and an LIG4 genotype is a normal or mutant type, and cultured in a 60 mm plate at $1 \times 10^5$ cells/well for 24 hours at 37° C. The cells were treated with 25 µM and 50 µM of Compound B, which is a novel PARP/Tankyrase simultaneous inhibitor, and olaparib, which is a competitive drug PARP inhibitor. After 48 hours of culturing, the change of cell shapes was analyzed to confirm the drug efficacy.

Experiment Result

Figure 20:
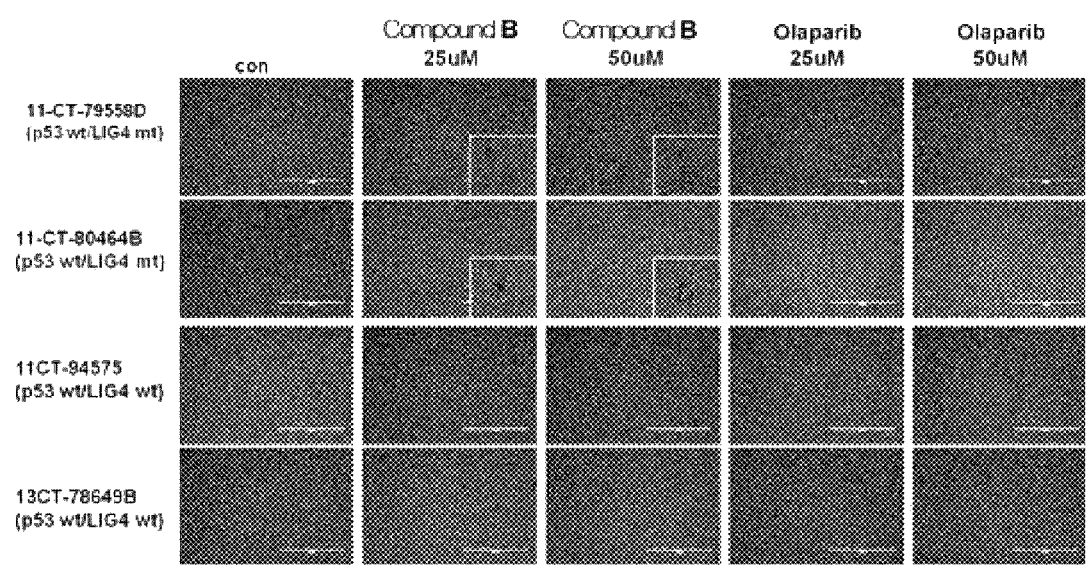
FIG. 20 shows the results of cell shape change analysis for the treatment of Compound B and olaparib, which are simultaneous inhibitors against PARP/Tankyrase, in colon cancer patients derived cells 11-CT-79558D (p53 WT/LIG4 MT), 11-CT-80464B (p53 WT/LIG4 MT) and 11CT-94575 (p53 WT/LIG4 WT), 13CT-78649B (p53 WT/LIG4 WT).

As a result of observing the degree of change in cell shape by treating the human colon cancer patient-derived cells in which a p53 genotype is a normal type and an LIG4 genotype is different with Compound B, which is a novel PARP/Tankyrase simultaneous inhibitor, and olaparib, which is a PARP inhibitor, using a microscope, it was observed that the cell shape for Compound B, which is a novel PARP/Tankyrase simultaneous inhibitor, died only in the colon cancer patient-derived cells 11-CT-79558D (p53 WT/LIG4 MT) and 11-CT-80464B (p53 WT/LIG4 MT) in which a p53 genotype is a normal type and an LIG4 genotype is a mutant type, and that there was no change in cell shape in olaparib, which is a PARP inhibitor, thus exhibiting drug reaction for apoptosis by Compound B only in case where a p53 is a normal type and an LIG4 is a mutant type (FIG. 20).

From the foregoing, the specific portions of the present disclosure have been described in detail. Therefore, it is apparent to a person having ordinary skill in the pertinent art that such specific technology is merely a preferable embodiment, and the scope of the present disclosure is not limited thereto. Accordingly, the substantial scope of the present disclosure is defined by the appended claims and their equivalents.

The invention claimed is:

1. A method for treating a human colorectal cancer patient having a normal type of the p53 gene and a mutant type of the LIG4 gene in a biological sample from the patient, comprising administering to said patient a therapeutically effective amount of [(dimethylamino)methyl]-10-ethoxy-1,2,3,4-tetrahydrobenzo[h][1,6]naphthyridin-5(6H)-one or 6-{4-[(5-oxo-1,2,3,4,5,6-hexahydrobenzo[h][1,6]naphthyridin-8-yl)methyl]piperazin-1-yl}nicotinonitrile.

2. The method according to claim 1, wherein the mutant type of the LIG4 gene is one or more sequence variants selected from the group consisting of a substitution of cytosine to thymine at position 8, a substitution of cytosine to thymine at position 26, a substitution of guanine to adenine at position 833 and a substitution of thymine to cytosine at position 1704 of SEQ ID NO: 2.

3. The method according to claim 1, wherein the mutant type of the LIG4 gene is one or more sequence variants selected from the group consisting of a substitution of alanine to valine at position 3, a substitution of threonine to isoleucine at position 9, a substitution of arginine to histidine at position 278 and a substitution of thymine of aspartic acid (GAT) to cytosine at position 568 of SEQ ID NO: 3.

4. The method according to claim 1, further comprising:
  (a) isolating or having isolated cells from the biological sample;
  (b) isolating or having isolated nucleic acid molecules of the cells of the step (a); and
  (c) detecting that the genotype of the p53 gene is a normal type and the genotype of the LIG4 gene is a mutant type, by using a primer or a probe that specifically binds to a nucleotide sequence encoding a p53 gene and a primer or a probe that specifically binds to a nucleotide sequence encoding an LIG4 (DNA ligase 4).

* * * * *

SEQUENCE LISTING

```
<160> NUMBER OF SEQ ID NOS: 13

<210> SEQ ID NO 1
<211> LENGTH: 1182
<212> TYPE: DNA
<213> ORGANISM: Homo sapiens

<400> SEQUENCE: 1
atggaggagc cgcagtcaga tcctagcgtc gagcccctc tgagtcagga aacattttca      60
gacctatgga aactacttcc tgaaaacaac gttctgtccc ccttgccgtc ccaagcaatg    120
gatgatttga tgctgtcccc ggacgatatt gaacaatggt tcactgaaga cccaggtcca    180
gatgaagctc ccagaatgcc agaggctgct cccccgtgg ccctgcacc agcagctcct     240 acaccggcgg ccctgcacc agcccctcc tggccctgt catcttctgt ccttcccag       300 aaaacctacc agggcagcta cggtttccgt ctgggcttct tgcattctgg gacagccaag   360
tctgtgactt gcacgtactc ccctgccctc aacaagatgt tttgccaact ggccaagacc   420
tgccctgtgc agctgtgggt tgattccaca cccccgcccg gcacccgcgt ccgcgccatg   480
gccatctaca agcagtcaca gcacatgacg gaggttgtga ggcgctgccc ccaccatgag   540
cgctgctcag atagcgatgg tctggcccct cctcagcatc ttatccgagt ggaaggaaat   600
ttgcgtgtgg agtatttgga tgacagaaac acttttcgac atagtgtggt ggtgccctat   660
gagccgcctg aggttggctc tgactgtacc accatccact acaactacat gtgtaacagt   720
tcctgcatgg gcggcatgaa ccggaggccc atcctcacca tcatcacact ggaagactcc   780
agtggtaatc tactgggacg gaacagcttt gaggtgcgtg tttgtgcctg tcctgggaga   840
gaccggcgca cagaggaaga gaatctccgc aagaaagggg agcctcacca cgagctgccc   900
ccagggagca ctaagcgagc actgcccaac aacaccagct cctctcccca gccaaagaag   960
aaaccactgg atggagaata tttcacccct cagatccgtg ggcgtgagcg cttcgagatg  1020
ttccgagagc tgaatgaggc cttggaactc aaggatgccc aggctgggaa ggagccaggg  1080
gggagcaggg ctcactccag ccacctgaag tccaaaaagg gtcagtctac ctcccgccat  1140
aaaaaactca tgttcaagac agaagggcct gactcagact ga                     1182

<210> SEQ ID NO 2
<211> LENGTH: 2736
<212> TYPE: DNA
<213> ORGANISM: Homo sapiens

<400> SEQUENCE: 2
atggctgcct cacaaacttc acaaactgtt gcatctcacg ttccttttgc agatttgtgt     60
tcaactttag aacgaataca gaaagtaaa ggacgtgcag aaaaaatcag acacttcagg   120
gaatttttag attcttggag aaaatttcat gatgctcttc ataagaacca caagatgtc    180 acagactctt tttatccagc aatgagacta attcttcctc agctagaaag agagagaatg   240
```

```
gcctatggaa ttaaagaaac tatgcttgct aagctttata ttgagttgct taatttacct    300
agagatggaa aagatgccct caaactttta aactacagaa cacccactgg aactcatgga    360
gatgctggag actttgcaat gattgcatat tttgtgttga agccaagatg tttacagaaa    420
ggaagtttaa ccatacagca agtaaacgac cttttagact caattgccag caataattct    480
gctaaagaa  aagacctaat aaaaagagc  cttcttcaac ttataactca gagttcagca    540
cttgagcaaa agtggcttat acggatgatc ataaaggatt taaagcttgg tgttagtcag    600
caaactatct tttctgtttt tcataatgat gctgctgagt tgcataatgt cactacagat    660
ctggaaaaag tctgtaggca actgcatgat ccttctgtag gactcagtga tatttctatc    720
actttatttt ctgcatttaa accaatgcta gctgctattg cagatattga gcacattgag    780
aaggatatga acatcagag  tttctacata gaaaccaagc tagatggtga acgtatgcaa    840
atgcacaaag atggagatgt atataaatac ttctctcgaa atggatataa ctacactgat    900
cagtttggtg cttctcctac tgaaggttct cttaccccat tcattcataa tgcattcaaa    960
gcagatatac aaatctgtat tcttgatggt gagatgatgg cctataatcc taatacacaa   1020
actttcatgc aaaagggaac taagtttgat attaaaagaa tggtagagga ttctgatctg   1080
caaacttgtt attgtgtttt tgatgtattg atggttaata ataaaaagct agggcatgag   1140
actctgagaa agaggtatga gattcttagt agtatttta  caccaattcc aggtagaata   1200
gaaatagtgc agaaaacaca agctcatact aagaatgaag taattgatgc attgaatgaa   1260
gcaatagata aagagaaga  gggaattatg gtaaaacaac ctctatccat ctacaagcca   1320
gacaaaagag gtgaagggtg gttaaaaatt aaaccagagt atgtcagtgg actaatggat   1380
gaattggaca ttttaattgt tggaggatat tggggtaaag gatcacgggg tggaatgatg   1440
tctcattttc tgtgtgcagt agcagagaag ccccctcctg gtgagaagcc atctgtgttt   1500
catactctct ctcgtgttgg gtctggctgc accatgaaag aactgtatga tctgggtttg   1560
aaattggcca agtattggaa gccttttcat agaaaagctc caccaagcag cattttatgt   1620
ggaacagaga agccagaagt atacattgaa ccttgtaatt ctgtcattgt tcagattaaa   1680
gcagcagaga tcgtacccag tgatatgtat aaaaactggct gcaccttgcg ttttccacga   1740
attgaaaaga taagagatga caaggagtgg catgagtgca tgaccctgga cgacctagaa   1800
caacttaggg ggaaggcatc tggtaagctc gcatctaaac acctttatat aggtggtgat   1860
gatgaaccac aagaaaaaaa gcggaaagct gccccaaaga tgaagaaagt tattggaatt   1920
attgagcact aaaagcacc  taaccttact aacgttaaca aaatttctaa tatatttgaa   1980
gatgtagagt tttgtgttat gagtggaaca gatagccagc caaagcctga cctggagaac   2040
agaattgcag aatttggtgg ttatatagta caaaatccag gcccagacac gtactgtgta   2100
attgcagggt ctgagaacat cagagtgaaa aacataattt tgtcaaataa acatgatgtt   2160
gtcaagcctg catggctttt agaatgtttt aagaccaaaa gctttgtacc atggcagcct   2220
cgctttatga ttcatatgtg cccatcaacc aaagaacatt tgcccgtga  atatgattgc   2280
tatggtgata gttatttcat tgatacagac ttgaaccaac tgaaggaagt attctcagga   2340
attaaaaatt ctaacgagca gactcctgaa gaaatggctt ctctgattgc tgatttagaa   2400
tatcggtatt cctgggattg ctctcctctc agtatgtttc gacgccacac cgtttatttg   2460
gactcgtatg ctgttattaa tgacctgagt accaaaaatg aggggacaag gttagctatt   2520
aaagccttgg agcttcggtt tcatggagca aaagtagttt cttgtttagc tgagggagtg   2580
tctcatgtaa taattgggga agatcatagt cgtgttgcag attttaaagc ttttagaaga   2640
```

```
acttttaaga gaaagtttaa aatcctaaaa gaaagttggg taactgattc aatagacaag   2700
tgtgaattac aagaagaaaa ccagtatttg atttaa                             2736
```

<210> SEQ ID NO 3
<211> LENGTH: 911
<212> TYPE: PRT
<213> ORGANISM: Homo sapiens

<400> SEQUENCE: 3

```
Met Ala Ala Ser Gln Thr Ser Gln Thr Val Ala Ser His Val Pro Phe
 1               5                  10                  15

Ala Asp Leu Cys Ser Thr Leu Glu Arg Ile Gln Lys Ser Lys Gly Arg
            20                  25                  30

Ala Glu Lys Ile Arg His Phe Arg Glu Phe Leu Asp Ser Trp Arg Lys
        35                  40                  45

Phe His Asp Ala Leu His Lys Asn His Lys Asp Val Thr Asp Ser Phe
    50                  55                  60

Tyr Pro Ala Met Arg Leu Ile Leu Pro Gln Leu Glu Arg Glu Arg Met
65                  70                  75                  80

Ala Tyr Gly Ile Lys Glu Thr Met Leu Ala Lys Leu Tyr Ile Glu Leu
                85                  90                  95

Leu Asn Leu Pro Arg Asp Gly Lys Asp Ala Leu Lys Leu Leu Asn Tyr
            100                 105                 110

Arg Thr Pro Thr Gly Thr His Gly Asp Ala Gly Asp Phe Ala Met Ile
        115                 120                 125

Ala Tyr Phe Val Leu Lys Pro Arg Cys Leu Gln Lys Gly Ser Leu Thr
    130                 135                 140

Ile Gln Gln Val Asn Asp Leu Leu Asp Ser Ile Ala Ser Asn Asn Ser
145                 150                 155                 160

Ala Lys Arg Lys Asp Leu Ile Lys Lys Ser Leu Leu Gln Leu Ile Thr
                165                 170                 175

Gln Ser Ser Ala Leu Glu Gln Lys Trp Leu Ile Arg Met Ile Ile Lys
            180                 185                 190

Asp Leu Lys Leu Gly Val Ser Gln Gln Thr Ile Phe Ser Val Phe His
        195                 200                 205

Asn Asp Ala Ala Glu Leu His Asn Val Thr Thr Asp Leu Glu Lys Val
    210                 215                 220

Cys Arg Gln Leu His Asp Pro Ser Val Gly Leu Ser Asp Ile Ser Ile
225                 230                 235                 240

Thr Leu Phe Ser Ala Phe Lys Pro Met Leu Ala Ala Ile Ala Asp Ile
                245                 250                 255

Glu His Ile Glu Lys Asp Met Lys His Gln Ser Phe Tyr Ile Glu Thr
            260                 265                 270

Lys Leu Asp Gly Glu Arg Met Gln Met His Lys Asp Gly Asp Val Tyr
        275                 280                 285

Lys Tyr Phe Ser Arg Asn Gly Tyr Asn Tyr Thr Asp Gln Phe Gly Ala
    290                 295                 300

Ser Pro Thr Glu Gly Ser Leu Thr Pro Phe Ile His Asn Ala Phe Lys
305                 310                 315                 320

Ala Asp Ile Gln Ile Cys Ile Leu Asp Gly Glu Met Met Ala Tyr Asn
                325                 330                 335

Pro Asn Thr Gln Thr Phe Met Gln Lys Gly Thr Lys Phe Asp Ile Lys
            340                 345                 350
```

```
Arg Met Val Glu Asp Ser Asp Leu Gln Thr Cys Tyr Cys Val Phe Asp
            355                 360                 365
Val Leu Met Val Asn Asn Lys Lys Leu Gly His Glu Thr Leu Arg Lys
370                 375                 380
Arg Tyr Glu Ile Leu Ser Ser Ile Phe Thr Pro Ile Pro Gly Arg Ile
385                 390                 395                 400
Glu Ile Val Gln Lys Thr Gln Ala His Thr Lys Asn Glu Val Ile Asp
                405                 410                 415
Ala Leu Asn Glu Ala Ile Asp Lys Arg Glu Gly Ile Met Val Lys
                420                 425                 430
Gln Pro Leu Ser Ile Tyr Lys Pro Asp Lys Arg Gly Glu Gly Trp Leu
            435                 440                 445
Lys Ile Lys Pro Glu Tyr Val Ser Gly Leu Met Asp Glu Leu Asp Ile
450                 455                 460
Leu Ile Val Gly Gly Tyr Trp Gly Lys Gly Ser Arg Gly Gly Met Met
465                 470                 475                 480
Ser His Phe Leu Cys Ala Val Ala Glu Lys Pro Pro Gly Glu Lys
                485                 490                 495
Pro Ser Val Phe His Thr Leu Ser Arg Val Gly Ser Gly Cys Thr Met
            500                 505                 510
Lys Glu Leu Tyr Asp Leu Gly Leu Lys Leu Ala Lys Tyr Trp Lys Pro
            515                 520                 525
Phe His Arg Lys Ala Pro Pro Ser Ser Ile Leu Cys Gly Thr Glu Lys
            530                 535                 540
Pro Glu Val Tyr Ile Glu Pro Cys Asn Ser Val Ile Val Gln Ile Lys
545                 550                 555                 560
Ala Ala Glu Ile Val Pro Ser Asp Met Tyr Lys Thr Gly Cys Thr Leu
                565                 570                 575
Arg Phe Pro Arg Ile Glu Lys Ile Arg Asp Asp Lys Glu Trp His Glu
            580                 585                 590
Cys Met Thr Leu Asp Asp Leu Glu Gln Leu Arg Gly Lys Ala Ser Gly
            595                 600                 605
Lys Leu Ala Ser Lys His Leu Tyr Ile Gly Gly Asp Asp Glu Pro Gln
610                 615                 620
Glu Lys Lys Arg Lys Ala Ala Pro Lys Met Lys Lys Val Ile Gly Ile
625                 630                 635                 640
Ile Glu His Leu Lys Ala Pro Asn Leu Thr Asn Val Asn Lys Ile Ser
                645                 650                 655
Asn Ile Phe Glu Asp Val Glu Phe Cys Val Met Ser Gly Thr Asp Ser
                660                 665                 670
Gln Pro Lys Pro Asp Leu Glu Asn Arg Ile Ala Glu Phe Gly Gly Tyr
            675                 680                 685
Ile Val Gln Asn Pro Gly Pro Asp Thr Tyr Cys Val Ile Ala Gly Ser
            690                 695                 700
Glu Asn Ile Arg Val Lys Asn Ile Ile Leu Ser Asn Lys His Asp Val
705                 710                 715                 720
Val Lys Pro Ala Trp Leu Leu Glu Cys Phe Lys Thr Lys Ser Phe Val
                725                 730                 735
Pro Trp Gln Pro Arg Phe Met Ile His Met Cys Pro Ser Thr Lys Glu
                740                 745                 750
His Phe Ala Arg Glu Tyr Asp Cys Tyr Gly Asp Ser Tyr Phe Ile Asp
            755                 760                 765
```

```
Thr Asp Leu Asn Gln Leu Lys Glu Val Phe Ser Gly Ile Lys Asn Ser
    770                 775                 780
Asn Glu Gln Thr Pro Glu Glu Met Ala Ser Leu Ile Ala Asp Leu Glu
785                 790                 795                 800
Tyr Arg Tyr Ser Trp Asp Cys Ser Pro Leu Ser Met Phe Arg Arg His
                805                 810                 815
Thr Val Tyr Leu Asp Ser Tyr Ala Val Ile Asn Asp Leu Ser Thr Lys
                820                 825                 830
Asn Glu Gly Thr Arg Leu Ala Ile Lys Ala Leu Glu Leu Arg Phe His
            835                 840                 845
Gly Ala Lys Val Val Ser Cys Leu Ala Glu Gly Val Ser His Val Ile
        850                 855                 860
Ile Gly Glu Asp His Ser Arg Val Ala Asp Phe Lys Ala Phe Arg Arg
865                 870                 875                 880
Thr Phe Lys Arg Lys Phe Lys Ile Leu Lys Glu Ser Trp Val Thr Asp
                885                 890                 895
Ser Ile Asp Lys Cys Glu Leu Gln Glu Glu Asn Gln Tyr Leu Ile
            900                 905                 910

<210> SEQ ID NO 4
<211> LENGTH: 19
<212> TYPE: RNA
<213> ORGANISM: Artificial Sequence
<220> FEATURE:
<223> OTHER INFORMATION: ATR siRNA

<400> SEQUENCE: 4
gaguucucag aagucaacc                                                  19

<210> SEQ ID NO 5
<211> LENGTH: 21
<212> TYPE: RNA
<213> ORGANISM: Artificial Sequence
<220> FEATURE:
<223> OTHER INFORMATION: XLF siRNA

<400> SEQUENCE: 5
cgcugauucg agaucgauug a                                               21

<210> SEQ ID NO 6
<211> LENGTH: 21
<212> TYPE: RNA
<213> ORGANISM: Artificial Sequence
<220> FEATURE:
<223> OTHER INFORMATION: XRCC4 siRNA

<400> SEQUENCE: 6
cugaucucuc uggguuggcu u                                               21

<210> SEQ ID NO 7
<211> LENGTH: 19
<212> TYPE: RNA
<213> ORGANISM: Artificial Sequence
<220> FEATURE:
<223> OTHER INFORMATION: LIG4 siRNA

<400> SEQUENCE: 7
gggagugucu cauguaaua                                                  19
```

```
<210> SEQ ID NO 8
<211> LENGTH: 26
<212> TYPE: DNA
<213> ORGANISM: Artificial Sequence
<220> FEATURE:
<223> OTHER INFORMATION: LIG4 Exon2-1 Forward primer

<400> SEQUENCE: 8
gctagctgct attgcagata ttgagc                                        26

<210> SEQ ID NO 9
<211> LENGTH: 26
<212> TYPE: DNA
<213> ORGANISM: Artificial Sequence
<220> FEATURE:
<223> OTHER INFORMATION: LIG4 Exon2-1 Reverse primer

<400> SEQUENCE: 9
agaaccttca gtaggagaag caccaa                                        26

<210> SEQ ID NO 10
<211> LENGTH: 20
<212> TYPE: DNA
<213> ORGANISM: Artificial Sequence
<220> FEATURE:
<223> OTHER INFORMATION: LIG4 Exon2-2 Forward primer

<400> SEQUENCE: 10
cctggtgaga agccatctgt                                               20

<210> SEQ ID NO 11
<211> LENGTH: 20
<212> TYPE: DNA
<213> ORGANISM: Artificial Sequence
<220> FEATURE:
<223> OTHER INFORMATION: LIG4 Exon2-2 Reverse primer

<400> SEQUENCE: 11
gccttccccc taagttgttc                                               20

<210> SEQ ID NO 12
<211> LENGTH: 29
<212> TYPE: DNA
<213> ORGANISM: Artificial Sequence
<220> FEATURE:
<223> OTHER INFORMATION: LIG4 Exon1-1 Forward primer

<400> SEQUENCE: 12
ttgctttact agttaaacga gaagattca                                     29

<210> SEQ ID NO 13
<211> LENGTH: 27
<212> TYPE: DNA
<213> ORGANISM: Artificial Sequence
<220> FEATURE:
<223> OTHER INFORMATION: LIG4 Exon1-1 Reverse primer

<400> SEQUENCE: 13
ttcgttctaa agttgaacac aaatctg                                       27
```